US012569306B2

(12) United States Patent
Facchinello et al.

(10) Patent No.: US 12,569,306 B2
(45) Date of Patent: Mar. 10, 2026

(54) ROBOTIC REVISION KNEE ARTHROPLASTY VIRTUAL RECONSTRUCTION SYSTEM

(71) Applicant: Orthosoft ULC, Montreal (CA)

(72) Inventors: Yann Facchinello, Prévost (CA); Vincent Pelletier, Montreal (CA); Adam H. Sanford, Minneapolis, MN (US); Catherine Leveille, Longueuil (CA); Adam D. Henderson, Winterthur (CH)

(73) Assignee: Orthosoft ULC

( * ) Notice: Subject to any disclaimer, the term of this patent is extended or adjusted under 35 U.S.C. 154(b) by 863 days.

(21) Appl. No.: 17/864,682

(22) Filed: Jul. 14, 2022

(65) Prior Publication Data

US 2023/0013210 A1 Jan. 19, 2023

Related U.S. Application Data

(60) Provisional application No. 63/231,070, filed on Aug. 9, 2021, provisional application No. 63/223,329, filed on Jul. 19, 2021.

(51) Int. Cl.
| | |
|---|---|
| *A61B 34/30* | (2016.01) |
| *A61B 17/16* | (2006.01) |

(Continued)

(52) U.S. Cl.
CPC .......... *A61B 34/30* (2016.02); *A61B 17/1675* (2013.01); *A61B 34/10* (2016.02);
(Continued)

(58) Field of Classification Search
CPC ... A61B 17/164; A61B 17/1675; A61B 34/10; A61B 2034/102; A61B 2034/105;
(Continued)

(56) References Cited

U.S. PATENT DOCUMENTS

| | | |
|---|---|---|
| 5,769,092 A | 6/1998 | Williamson, Jr. |
| 10,194,991 B2 | 2/2019 | Bonny et al. |

(Continued)

FOREIGN PATENT DOCUMENTS

| | | |
|---|---|---|
| EP | 1870053 B1 | 12/2009 |
| WO | 2020163314 | 8/2020 |
| WO | WO-2021067922 A1 | 4/2021 |

OTHER PUBLICATIONS

Giordano, Md, Gerard, et al., "ExactechGPS RTKA Operative Technique", Exactech, Inc. 712-32-30 Rev. B 0621, (2021), 50 pgs.

(Continued)

*Primary Examiner* — Larry E Waggle, Jr.
(74) *Attorney, Agent, or Firm* — SCHWEGMAN LUNDBERG & WOESSNER, P.A.

(57) ABSTRACT

Systems that may be used for performing a robotic revision knee arthroplasty are disclosed. Such systems can optionally include a processor that can: intraoperatively receive a plurality of position data obtained by a robotic surgical device after a primary implant has been removed from a bone, the plurality of position data correspond to a plurality of landmarks of the bone of a patient, the plurality of landmarks include a position of an intramedullary canal of the bone; select from a database having a plurality of mean models of a corresponding bone a mean model that comprises a best match based upon the plurality of landmarks of the bone: generate an updated model by altering the mean model to fit an anatomy of the bone of the patient based upon the plurality of landmarks; and output to a user interface the updated model for use during the robotic revision knee arthroplasty.

19 Claims, 17 Drawing Sheets

(51) Int. Cl.

| | |
|---|---|
| *A61B 34/00* | (2016.01) |
| *A61B 34/10* | (2016.01) |
| *A61B 34/20* | (2016.01) |
| *A61B 34/37* | (2016.01) |
| *A61F 2/46* | (2006.01) |
| *A61B 90/00* | (2016.01) |
| *A61F 2/30* | (2006.01) |

(52) U.S. Cl.

CPC .............. *A61B 34/20* (2016.02); *A61B 34/25* (2016.02); *A61B 34/37* (2016.02); *A61F 2/461* (2013.01); *A61B 17/164* (2013.01); *A61B 2034/102* (2016.02); *A61B 2034/105* (2016.02); *A61B 2034/108* (2016.02); *A61B 2034/2072* (2016.02); *A61B 2034/252* (2016.02); *A61B 2034/254* (2016.02); *A61B 2090/365* (2016.02); *A61F 2002/3069* (2013.01); *A61F 2002/4632* (2013.01)

(58) Field of Classification Search

CPC ... A61B 2034/108; A61B 34/20; A61B 34/25; A61B 2034/252; A61B 2034/254; A61B 34/30; A61B 2090/365; A61F 2002/3069; A61F 2002/4632

See application file for complete search history.

(56) References Cited

U.S. PATENT DOCUMENTS

| | | | | |
|---|---|---|---|---|
| 10,265,127 | B2 | 4/2019 | Jaramaz et al. | |
| 10,716,630 | B2 | 7/2020 | Krebs et al. | |
| 10,932,866 | B1 | 3/2021 | Bonny et al. | |
| 11,364,081 | B2 * | 6/2022 | Dees, Jr. ................ | A61B 90/96 |
| 11,478,362 | B2 | 10/2022 | Thompson et al. | |
| 12,137,996 | B2 | 11/2024 | Boisvert et al. | |
| 12,150,657 | B2 * | 11/2024 | Greber ................... | A61B 34/20 |
| 2007/0270680 | A1 | 11/2007 | Sheffer et al. | |
| 2009/0102844 | A1 | 4/2009 | Deparis | |
| 2017/0265945 | A1 | 9/2017 | Jaramaz et al. | |
| 2017/0360509 | A1 | 12/2017 | Bonny et al. | |
| 2018/0014891 | A1 | 1/2018 | Krebs et al. | |
| 2018/0116739 | A1 | 5/2018 | Gogarty et al. | |
| 2020/0138518 | A1 | 5/2020 | Lang | |
| 2020/0222206 | A1 | 7/2020 | Elliot | |
| 2021/0038328 | A1 | 2/2021 | Boisvert et al. | |
| 2025/0032205 | A1 | 1/2025 | Boisvert et al. | |

OTHER PUBLICATIONS

"Canadian Application Serial No. 3,167,940, Examiners Rule 86(2) Report mailed Jul. 14, 2025", 11 pgs.

"European Application Serial No. 22185819.4, Response Filed Jul. 16, 2025 to Communication Pursuant to Article 94(3) EPC mailed Apr. 16, 2025", 64 pgs.

"European Application Serial No. 22185819.4, Extended European Search Report mailed Nov. 29, 2022", 10 pgs.

"U.S. Appl. No. 16/988,090, Restriction Requirement mailed May 31, 2023", 7 pgs.

"U.S. Appl. No. 16/988,090, Response filed Jul. 31, 2023 to Restriction Requirement mailed May 31, 2023", 6 pgs.

"European Application Serial No. 22185819.4, Response filed Jul. 25, 2023 to Extended European Search Report mailed Nov. 29, 2022", 27 pgs.

"U.S. Appl. No. 16/988,090, Non Final Office Action mailed Sep. 27, 2023", 9 pgs.

"Canadian Application Serial No. 3,167,940, Examiners Rule 86(2) Requisition mailed Oct. 5, 2023", 11 pgs.

"U.S. Appl. No. 16/988,090, Response filed Dec. 27, 2023 to Non Final Office Action mailed Sep. 27, 2023", 7 pgs.

"U.S. Appl. No. 16/988,090, Final Office Action mailed Feb. 23, 2024", 11 pgs.

"Canadian Application Serial No. 3,167,940, Response Filed Feb. 1, 2024 to Examiners Rule 86(2) Requisition mailed Oct. 5, 2023", 21 pgs.

"U.S. Appl. No. 16/988,090, Response filed Apr. 22, 2024 to Final Office Action mailed Feb. 23, 2024", 8 pgs.

"U.S. Appl. No. 16/988,090, Response filed May 20, 2024 to Final Office Action mailed Feb. 23, 2024", 9 pgs.

"U.S. Appl. No. 16/988,090, Advisory Action mailed May 23, 2024", 6 pgs.

"U.S. Appli. No. 16/988,090, Notice of Allowance mailed Jul. 9, 2024", 10 pgs.

"European Application Serial No. 22185819.4, Communication Pursuant to Article 94(3) EPC mailed Apr. 16, 2025", 9 pgs.

* cited by examiner 204, 210

150

204, 210

150

206

204

A

A

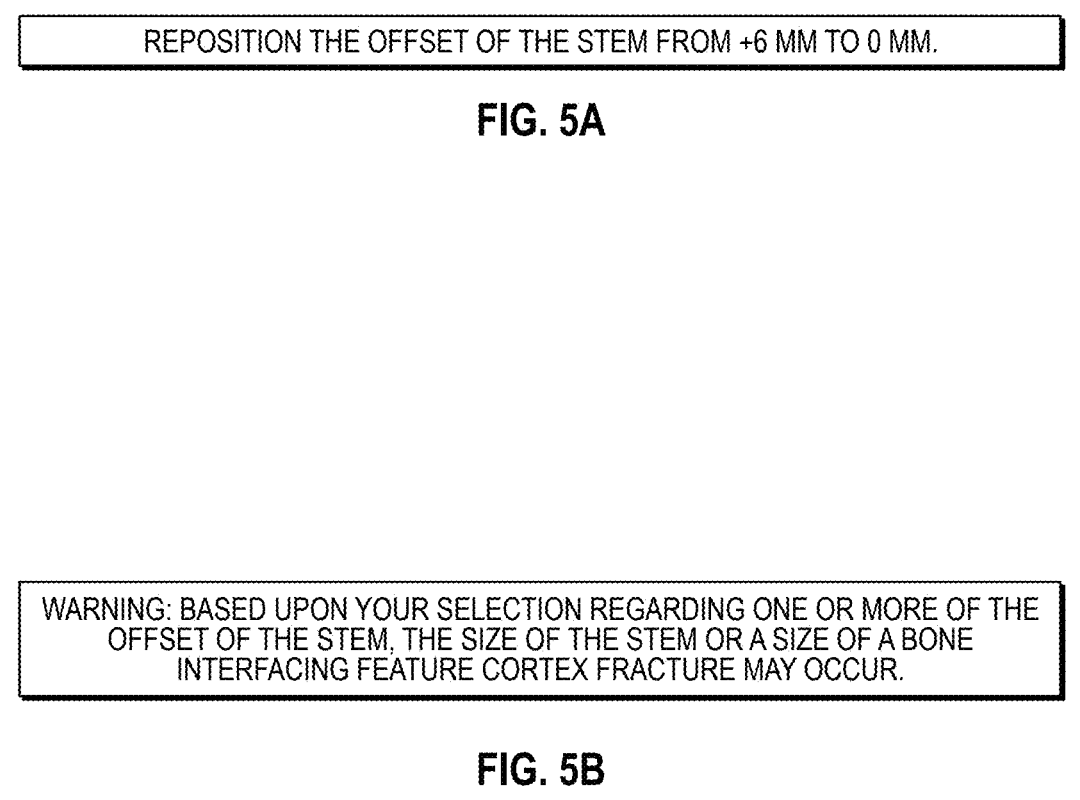

REPOSITION THE OFFSET OF THE STEM FROM +6 MM TO 0 MM.

FIG. 5A

WARNING: BASED UPON YOUR SELECTION REGARDING ONE OR MORE OF THE OFFSET OF THE STEM, THE SIZE OF THE STEM OR A SIZE OF A BONE INTERFACING FEATURE CORTEX FRACTURE MAY OCCUR.

FIG. 5B

FACTORS:
GENDER
MECHANICAL AXIS LENGTH
TRANS-EPICONDYLAR AXIS LENGTH
IM CANAL – MECHANICAL AXIS ANGLE IN SAGITTAL
PLANE
IM CANAL – MECHANICAL AXIS ANGLE IN FRONTAL
PLANE
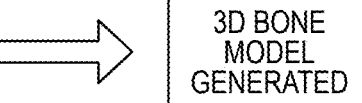
3D BONE
MODEL
GENERATED
FIG. 13
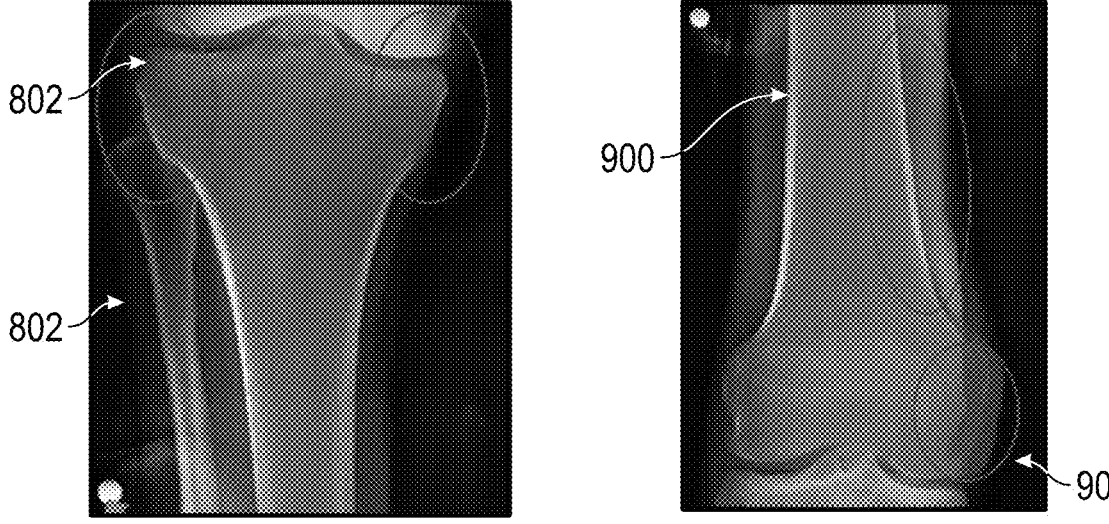
FIG. 14A                    FIG. 14B

1000

1002  INTRAOPERATIVELY RECEIVE A PLURALITY OF REFERENCE POINTS

1004  DETERMINE PERSONALIZED MODEL OF THE BONE BASED UPON LANDMARKS

1006  PLAN ROBOTIC REVISION ARTHROPLASTY USING PERSONALIZED MODEL

1408  DISPLAY PERSONALIZED MODEL WITH REVISION IMPLANT(S)

1010  DISPLAY LANDMARKS AS PART OF PERSONALIZED MODEL WITH THE IMPLANT(S)

ROBOTIC REVISION KNEE ARTHROPLASTY VIRTUAL RECONSTRUCTION SYSTEM

CLAIM OF PRIORITY

This application claims the benefit of U.S. Provisional Patent Application Ser. No. 63/223,329, filed on Jul. 19, 2021, and also claims the benefit of U.S. Provisional Patent Application Ser. No. 63/231,070, filed on Aug. 9, 2021, the benefit of priority of each of which is claimed hereby, and each of which is incorporated by reference herein in its entirety.

BACKGROUND

An implant revision surgery is a process by which an existing implant is removed to be replaced by a new implant. However, due to the bond between the implant to be removed and the bone, the bone is often damaged during implant removal. As a result, the subsequent positioning and installation of a replacement implant may lack precision due to damaged bone surfaces. For instance, in knee revision surgery, machining of the bone surfaces using conventional cutting blocks may lack precision as conventional bone landmarks used for defining the orientation of the cutting block may be altered or removed during the removal of the implant.

Computer-assisted surgery has been developed in order to help a surgeon in altering bones, and in positioning and orienting implants to a desired location. Computer-assisted surgery may encompass a wide range of devices, including surgical navigation, pre-operative planning, and various robotic devices. One area where computer-assisted surgery has potential is in orthopedic joint repair or replacement surgeries. Many conventional techniques (that do not use a robot, for example) may result in errors or may lack precision.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 5A and 5B show exemplary user prompts that can be issued in view of user's selections using the user interface of FIG. 5.

FIG. 13 shows a schematic of various anatomical factors including landmarks that can be used in generating a three-dimensional bone model in accordance with at least one example of this disclosure.

FIG. 14A shows a bone model displayed in conjunction with an image of the tibia of the patient in accordance with at least one example of this disclosure.

FIG. 14B shows a bone model displayed in conjunction with an image of the femur of the patient in accordance with at least one example of this disclosure.

DETAILED DESCRIPTION

Systems and methods for performing a revision knee arthroplasty using a robotic surgical device are described herein.

Revision surgery includes removing a previous implant and placing a new implant. In revision knee surgery, the native joint line cannot be re-created due to the removal of the underlying bone during a primary knee procedure. The systems and methods described herein use a robotic surgical device to assist in portions of the revision surgical process including in gathering reference points and generating a model that reconstructs of the anatomy of the patient. This model can reproduce the native joint line in a virtual space for the planning of the revision procedure. As an example, the robotic surgical device may be used to collect reference points along the bone, make measurements and perform other tasks as further discussed herein. The robotic surgical systems and methods may be used during pre-operative planning, assisting in virtual design of the revision implant, assisting in the placement of the new revision implant, or the like. Further functions can be performed by robotic surgical systems and methods as further discussed herein including providing the user with prompts, warnings, reminders, verification or the like. According to some examples the robotic surgical device can assist in removal of the existing implant, preparing of the bone surface, and implanting the new revision implant.

Use of the robotic surgical systems and methods may improve precision, for example, in accessing bone loss, in generating a plan in response to such bone loss and in improving selection, size and positioning of revision implants in response to the bone loss. Improvements include reducing the likelihood of human error. The robotic surgical system or method can implement predictive analytics or generate models of the bone of the patient. These can used to plan or replan the revision procedure including determining the size, position and type of the revision implant that be implanted. For example, based upon a virtual selection by the user regarding one or more of an offset of the stem, a size of the stem or a size of a bone interfacing feature (e.g. a keel, peg, etc.), the robotic surgical system or method can issue a warning that a breakage of the bone is likely to occur if such selection is implemented during the arthroplasty.

Figure 1:
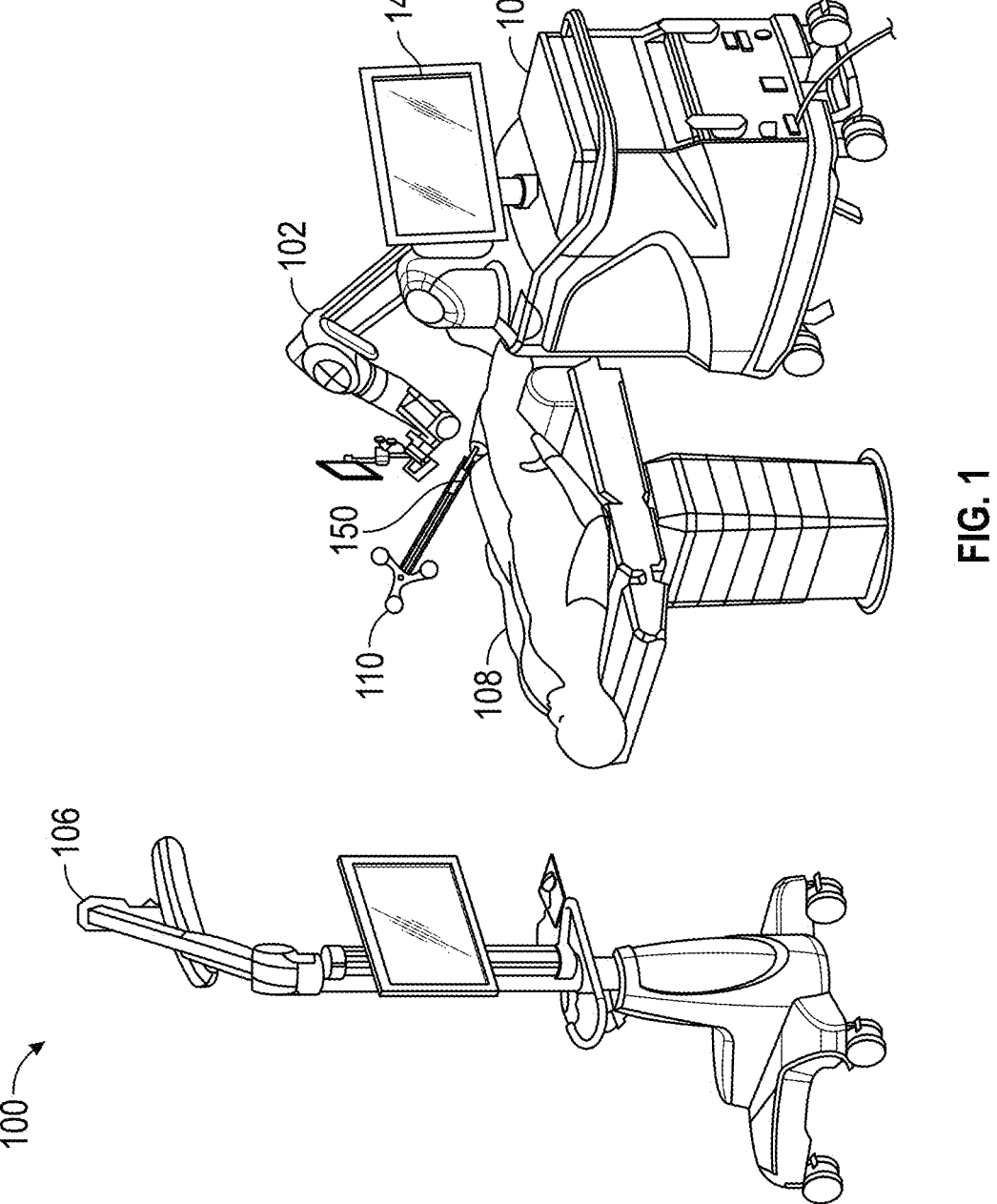
FIG. 1 is a schematic view of a robotic surgical system including a robotic surgical device (e.g., a robot or a robotic arm) and a computer (e.g., a device having a processor) in accordance with at least one example of this disclosure.

FIG. 1 illustrates a robotic surgical system 100 including a robotic surgical arm 102 (sometimes referred to herein a robotic surgical device) and a computing device 104 (e.g., a device having a processor) in accordance with at least one example of this disclosure. In an example, the robotic surgical device 102 and the computing device 104 may be coupled, such as communicatively coupled or physically connected.

The computing device 104 can include at least memory, a processing unit, and user input devices, as will be described herein. The computing device 104 can also include human interface device 145 for providing models and images for a surgeon to be used during surgery. The computing device 104 is illustrated as a separate standalone system, but in some examples computing device 104 can be integrated into robotic surgical system 100. Human interface device 145 can provide models and/or images, including but not limited to three-dimensional images of bones, joints, virtual implants, landmarks, and the like as further discussed herein. The human interface device 145 can include associated input mechanisms, such as a touch screen, wearable, mixed reality device, mouse, display, foot pedals, or other input and/or output devices compatible with a surgical environment.

The robotic surgical system 100 is for operation on surgical area of a patient 108 in accordance with at least one example of the present disclosure. Surgical area in one example can include a joint and, in another example, can be a bone. Surgical area can include any surgical area of patient, including but not limited to the shoulder, head, elbow, thumb, spine, and the like. However, aspects of the present application are directed to a knee arthroplasty procedure, and particular, to a revision knee arthroplasty. The robotic surgical system 100 can also include one or more robotic arms 102. As illustrated, robotic surgical system 100 can utilize only a single robotic arm. Robotic arm 102 can be a 6 degree-of-freedom (DOF) robot arm, such as the ROSA® robot from Medtech, a Zimmer Biomet Holdings, Inc. company. In some examples, robotic arm 102 is cooperatively controlled with surgeon input on the end effector or surgical instrument. In other examples, robotic arm 102 can operate autonomously. While not illustrated in FIG. 1, one or more positionable surgical support arms can be incorporated into robotic surgical system 100 to assist in positioning and stabilizing instruments or anatomy during various procedures.

While not shown in FIG. 1, the robotic arm 102 can rotate axially and radially and can receive a surgical instrument, or end effector, at a distal end. The surgical instrument can be any surgical instrument adapted for use by the robotic system, including, for example, a guide tube, a holder device, a gripping device such as a pincer grip, a burring device, a reaming device, cut guide, an impactor device such as a humeral head impactor, a pointer, a probe or the like. The surgical instrument can be positionable by robotic arm 102, which can include multiple robotic joints, that allow the surgical instrument to be positioned at any desired location adjacent or within a given surgical area.

As an instrument in FIG. 1, the robotic surgical system 100 optionally includes an optical navigation system 106, which may detect a location of an optical navigation device 110. The system 100 is shown in relation to the patient 108. As shown in FIG. 1, the patient 108 may be undergoing a revision knee procedure, for example to remove an existing implant and optionally receive a new implant. The robotic arm 102 may be used to perform aspects of the revision procedure as further discussed herein.

The robotic arm 102 can be separately registered to the coordinate system of the robotic surgical system 100, such via use of the navigation system 106. Fiducial markers (including those of the navigation device 110) can additionally be separately registered to the coordinate system of the robotic surgical system 100 via engagement with a probe having a tracking element attached thereto. As such, some or all of the components of the robotic surgical system 100 can be individually registered to the coordinate system and, if desired, movement of such components can be continuously or intermittently tracked with the navigation system 106.

In an example, a bone or bones (e.g., the tibia and femur) of the patient 108 may be modeled before an existing implant is removed. The current bone and implant model may be in a virtual two dimensional (2D) or three dimensional (3D) format. Such modeling of bone is discussed in further detail subsequently and can be based at least partial on the optical navigation system 106 and the optical navigation device 110. The modeling of the bone can also be based upon registration of the bone including landmarks thereof using a pointer, a probe or the like. In certain examples, the robotic surgical system 100 can also include a laser pointer that can generate a laser beam or array that is used for registration, identification, alignment of implants during surgical procedure, or the like. The modeling discussed herein need not be based upon pre-operative or intraoperative imaging of the bone using existing technology such as, but not limited to computed tomography (CT)

scans, magnetic resonance imaging (MRI), two-dimensional x-rays, three-dimensional x-rays, ultrasound, and the like.

However, according to some examples, the modeling can be based in whole, part or can be supplemented by such imaging. Imaging can also be used to supplement modeling such as by overlaying image of the bone on the model, for example. In another example, the bone model may have been previously generated during implantation of the primary implant. The one model may be obtained and updated from the primary implant procedure.

In an example, a model of the bone can include or be limited to certain bone landmarks of the bone as further discussed in detail subsequently. However, according to further examples the model can comprise further information such as a surface geometry of parts of the bone that are exposed despite the presence of the implant. The model of the bone may include a surface geometry of the possible suitable revision implants relative to one or more bone landmarks, adjacent bone surfaces, or the like. According to further examples, the model of the bone can include 2D or 3D geometry of the revision implant, for example using a 2D or 3D model of the implant (e.g., from the manufacturer, etc.).

The model of the bone with implant may comprise data pertaining to the surface geometry of a relevant portion of a bone and of the implant, including surfaces of the bone that are exposed despite the presence of the implant. The model of the bone with implant may also include landmark information (e.g. location display, confidence in the model at the landmark), full bone models with implants, axes, resections, center of rotations, etc). The model may also include a bone and revision implant planning model with an identification of implants that may be used, and bone alteration models (replanning) to receive the implants and other accessories based on surgical planning.

The bone modeling may include generating a 2D or 3D landmarks and/or the surface of the bone when the bone modeling is not directly performed by the imaging equipment, or if not complete. In an example in which multiple implants are to be replaced (e.g., a total knee revision), all bones supporting implants may be modeled. Additional structures may be modeled as well, such as cartilage, hip joint, hip, ankle, etc.

In terms of planning, an operator may select using the human interface device 145, a position or orientation of a 3D model of the revision implant (e.g., a new implant) relative to the bone as further discussed herein. In another example, the location or orientation the revision implant may be suggested or automatically generated (e.g., using machine learning). Planning may include various aspects including determining a location of bone resections to support the replacement implant, overlaying of the revision implants on the bone model, replanning based upon positioning and sizing of revision implant components selected, advice, warnings, reminders, or the like as further discussed herein. In another example the models described with respect to the patient anatomy need not be actually rendered or displayed. Instead, the models may be used by the robotic surgical system 100 to perform portions of a revision procedure. For example, coordinates of registered points (such and landmarks) and interpolated or extrapolated other points, simulation of coordinates as moved or revised during a procedure, or the like may be stored in memory. The robotic surgical system 100 may retrieve data stored in the memory when performing a portion of the revision procedure. In yet further embodiments, display may be performed on a mixed reality device such as eyewear worn by a surgeon performing the procedure.

In an example, an intramedullary reamer, rod or broach 150 may be implanted to reinforce or identify an intramedullary canal of a bone. The planning may include determining a position of the intramedullary rod (e.g., an orientation and/or 3D location) using the navigation system 106 and the navigation device 110. For example, the robotic surgical system 100 via the computing device 104 may identify an axis of the tibia (such as an anatomic and/or mechanical axis as shown in FIG. 1) or femur as determined by the navigation system 106 and the navigation device 110. The intramedullary rod can be placed by the robotic arm 102 or by conventional methods. For example, the medullary cavity may be hollowed out by the robotic arm 102. Additional information including location and/or orientation of the intramedullary canal or an epicondylar axis may be used as further discussed herein as one landmark.

In an example, the robotic surgical device 102 may be used to cut the bone, for example using a reference guide developed from the 3D model of the bone and the existing implant. The robotic surgical device may autonomously perform the cut (e.g., using the optical navigation system 106 to guide the robotic surgical device 102). The optical navigation system 106 may track the optical navigation device 110, which may be affixed to a bone or an implant of the patient, or affixed to a portion of the robotic surgical device 102. Several optical navigation devices (e.g., trackers) may be used, for example one on each of a femur, tibia, the robotic arm 102, and an existing implant. From the tracking information gathered by the optical navigation system 106, used to track each of the optical navigation devices, the robotic surgical device 102 may be guided to perform a cut (e.g., to remove the existing implant).

After the existing implant has been removed (by the surgeon or by the robotic arm 102 autonomously or collaboratively as a force assist device), the robotic arm 102, instruments as discussed above and/or the navigation system 106 may be used to reregister one or more landmarks of the bone, reregister a surface of the bone, or replan a new implant (e.g., modify a preoperative plan intraoperatively).

Various mean bone models and related software have been developed. Such mean bone models may be determined based on, or according to, data stored in an anatomic database. For example, ZiBRA™ Analytical Modeling System is one such an anatomic database from Zimmer, Inc., of Warsaw, Indiana. ZiBRA™ is a database used to collect and analyze anatomic data. The operating thesis for ZiBRA™ is that when used to design orthopedic components they will conform better to the anatomy and provide increased clinical options. The ZiBRA™ software application enables: statistical shape analysis, virtual surgery, component placement optimization, and implant fit assessment.

In an example, the computing device 104 may use a mean bone model such as one provided by the ZiBRA™ Analytical Modeling System. This modeling system can be stored in a planning subsystem of the robotic surgical system 100 or can otherwise be in communication therewith. Patient demographics (patient height, patient weight, patient gender, etc.) and bone landmarks (discussed subsequently) can be used to select an appropriate mean bone model from the modeling system. Optionally, preoperative imaging of the patient may aid in the selection of the mean bone model.

The computing device 104 can also be configured based upon landmarks and/or demographics to perform alteration, modification or deformation of the selected mean bone model. Such modification can be based upon bone landmarks, demographics, soft tissue or other information. Patient demographics can include patient height, patient weight, patient gender, or the like. This modification allows the computing device 104 to be predictive what anatomy of the patient's bone looked like (e.g., before the existing implant degraded, before the existing implant was put in, or before the existing implant was needed, such as when the bone was healthy). From the predicted anatomy, an updated model may be determined or kinematic information may be determined.

While the above examples provide a model generated intraoperatively, for example using registration and optical navigation. This model may not be a fully rendered 2D or 3D model of the patient anatomy, but may instead include landmarks (key reference points and/or axes), interpolated or extrapolated points, or other information used for completing a revision procedure. Further contemplated functionality includes that patient anatomy may be modeled preoperatively, and used to plan steps of a revision surgical procedure. Deviations from the plan may occur during the procedure, and modifications to the plan (e.g., replanning) may occur intraoperatively, particularly when using the robotic surgical system 100.

An example technique using the robotic arm 102 may include performing a cut to remove an existing implant (e.g., using traditional human technique or the robotic arm 102) as discussed in co-pending U.S. Ser. No. 16/988,090, the entire specification of which is incorporated herein by reference. Following implant removal, the quality of the preserved underlying bone is unpredictable. The navigation subsystem of the robotic surgical system 100 can be used to capture data points (also called data points or landmarks herein) from the surface of the bone. These data points are used to deform the mean bone model to fit the patient's anatomy more precisely. Thus, the robotic surgical technique may include mapping data points of an existing bone surface (e.g., an articular surface, one or more axes), and predicting the surface in a prior state.

The deformed bone model can be used to determine an approximation of the native joint line of the patient, which is beneficial to planning the revision surgery. Based upon the joint line, the robotic surgical system 100 may be used to determine a level of constraint appropriate, model kinematics and perform other tasks as discussed in U.S. Ser. No. 16/988,090. For example, with a particular amount of laxity detected by the robotic arm 102, a corresponding level of constraint may be used. The level of constraint may be determined based on how much constraint the component system provides due to the loss of ligament or patient anatomy (e.g., hinges are a high level of constraint, posterior stabilized may be a lower level of constraint).

Figure 2B:
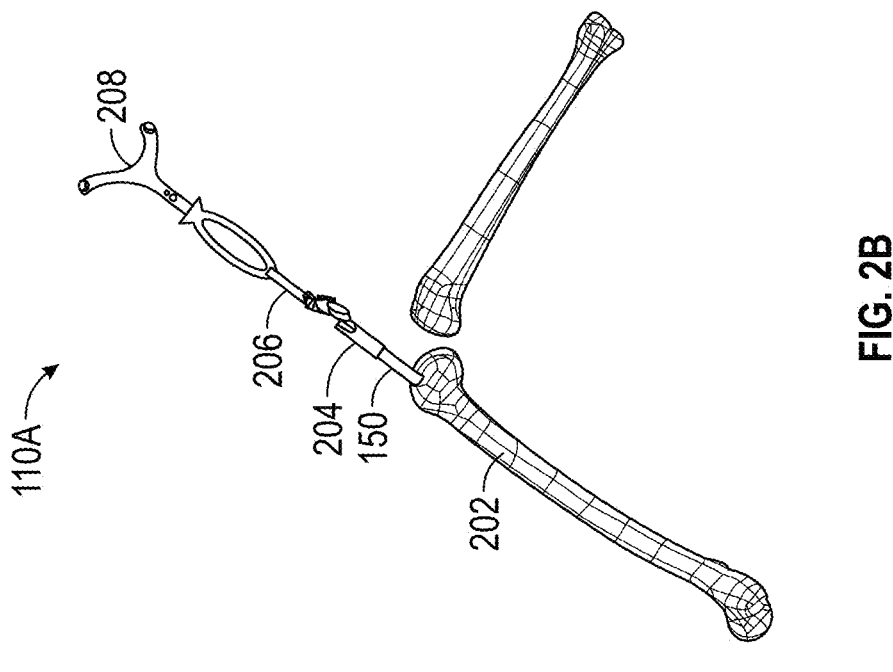
FIG. 2B is a plan view of the navigation tool assembly mounted to a femur of a patient undergoing a revision knee arthroplasty to determine a position of an intramedullary canal of the femur in accordance with at least one example of this disclosure.
Figure 2A:
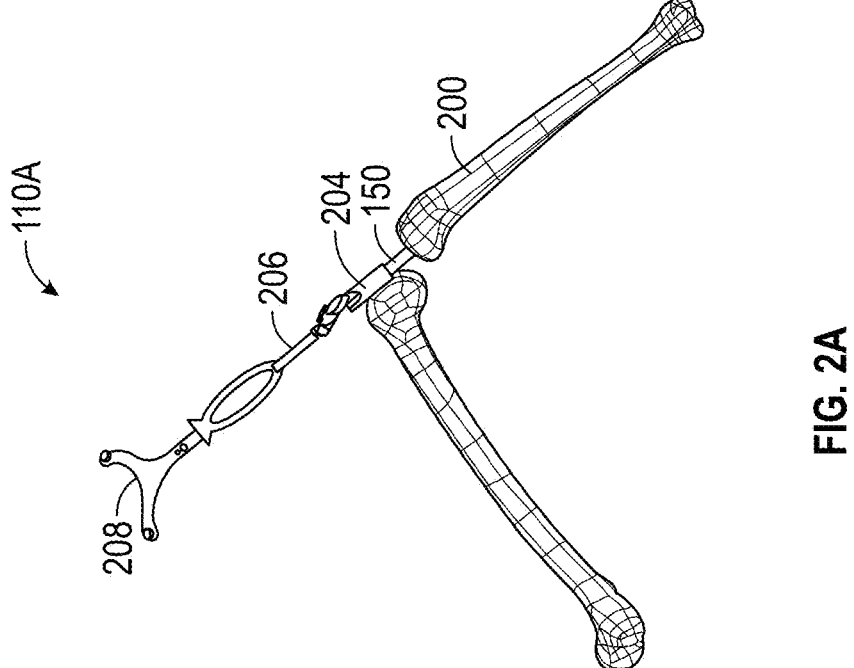
FIG. 2A is a plan view of a navigation tool assembly mounted to a tibia of a patient undergoing a revision to determine a position of an intramedullary canal of the tibia in accordance with at least one example of this disclosure.

FIGS. 2A and 2B illustrate an example of a navigation device 110A of similar to configuration that of the navigation device 110 discussed previously. As shown in FIG. 2A, the navigation device 110A can be mounted to the intramedullary reamer, rod or broach 150 inserted in the intramedullary canal of a tibia 200 of the patient. FIG. 2B shows the navigation device 110A can be mounted to the intramedullary reamer, rod or broach 150 inserted in the intramedullary canal of the femur 202 of the patient.

In the example of FIGS. 2A and 2B, the navigation device 110A can include a coupling 204, a shaft 206 and a navigation tracker 208. The coupling 204 can be configured to receive or otherwise couple with the intramedullary reamer, rod or broach 150. As such, the coupling 204 can be provided in different sizes corresponding to the size of the intramedullary reamer, rod or broach 150. The coupling 204 can be configured to selectively detached from and attached to the shaft 206. The shaft 206 can connect with the navigation tracker 208. According to the examples of FIGS. 2A and 2B, the navigation tracker 208 can be provide with three dots or other shapes or indicia of a known size and 3D position (orientation and 3D location) relative to one another. An existing optical tracking system (e.g., such as that of navigation system 106 using a camera) at a known distance can track the position of the three dots on the navigation tracker 208. From this information a processor can determine the position of the navigation device 110A. Alternatively, the navigation tracker 208 can be contacted with a probe, pointer or the like, in another manner to register the position of the navigation device 110A without using an optical system.

Figure 3A:
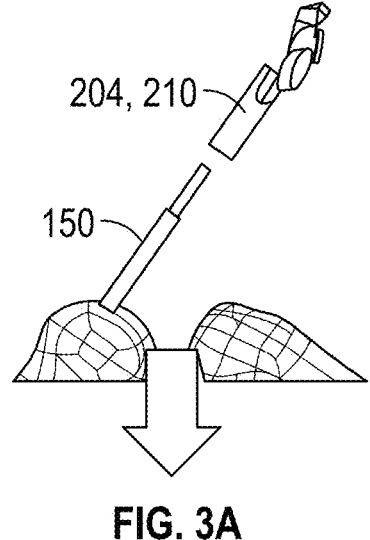
FIGS. 3A and 3B are perspective views of components of the navigation tool assembly coupling to an intramedullary reamer, rod or broach in accordance with at least one example of this disclosure.
Figure 3B:
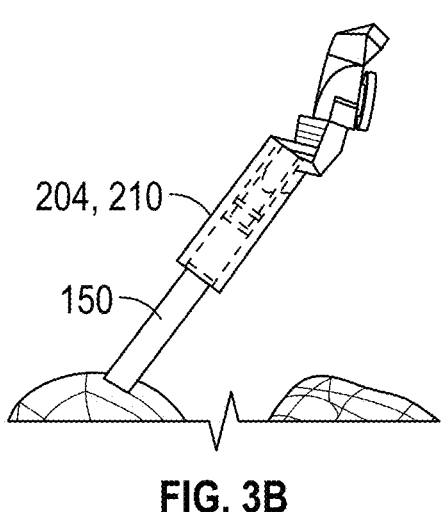

FIGS. 3A and 3B illustrate a process whereby the coupling 204 is attached with the intramedullary reamer, rod or broach 150. The coupling 204 is configured as a sleeve 210 to receive the intramedullary reamer, rod or broach 150.

Figure 4A:
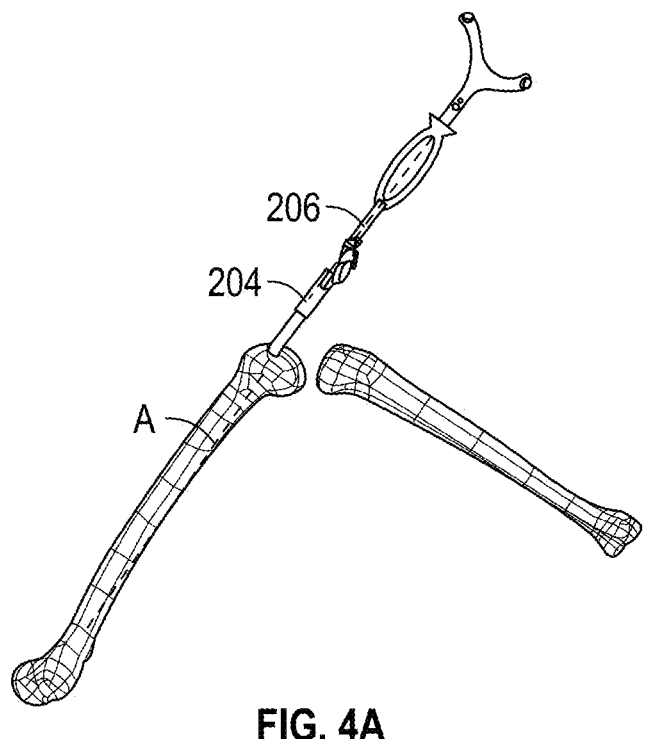
FIG. 4A is a first plan view that shows an axis of the femur as approximated using the position of an intramedullary canal of the femur as determined using the navigation tool assembly in accordance with at least one example of this disclosure.
Figure 4B:
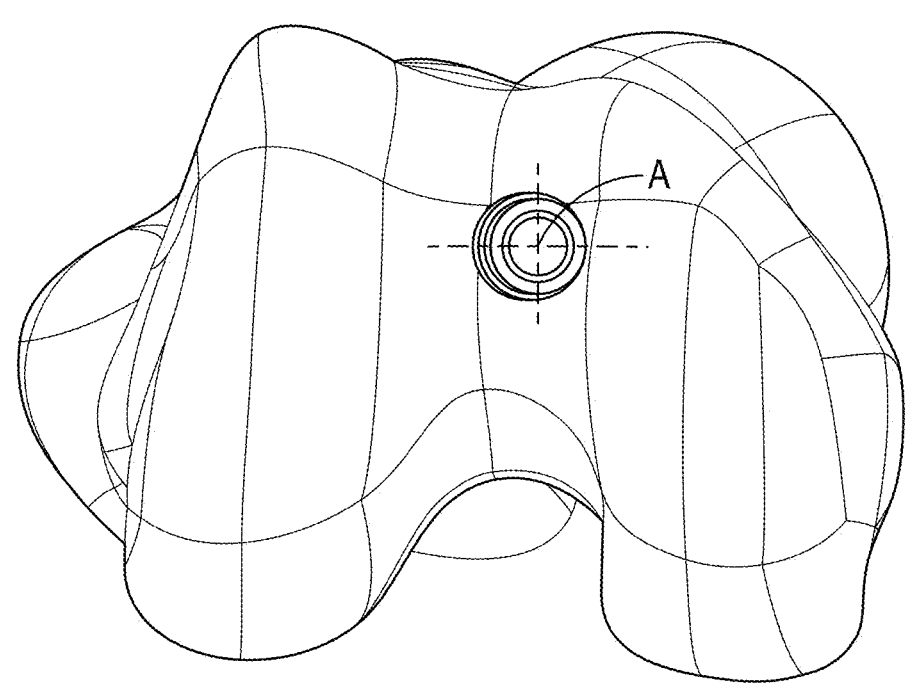
FIG. 4B is a second plan view of the axis of the femur using the position of an intramedullary canal of the femur as determined using the navigation tool assembly in accordance with at least one example of this disclosure.

The longitudinal axis of the intramedullary reamer, rod or broach 150 approximates the intramedullary canal as the intramedullary reamer, rod or broach 150 is inserted therein. As the intramedullary canal extends along the axis A (anatomic and/or mechanical axis) of the femur 202, the longitudinal axis of the intramedullary reamer, rod or broach 150 aligns with the axis A of the femur 202 as shown FIGS. 4A and 4B. The coupling 204 can be configured to receive the intramedullary reamer, rod or broach 150 such that longitudinal axes of the shaft 206 and the coupling 204 are coincident with a longitudinal axis of the intramedullary reamer, rod or broach 150 as shown in FIG. 4A. In this manner, once the processor determines the position of the navigation device 110A, the position (orientation and 3D location) of the axis A of the femur 202 can also be determined as shown in FIGS. 4A and 4B. The axis (anatomic and/or mechanical axis) of the tibia 200 (FIG. 2A) can be determined in a similar manner.

Figure 5:
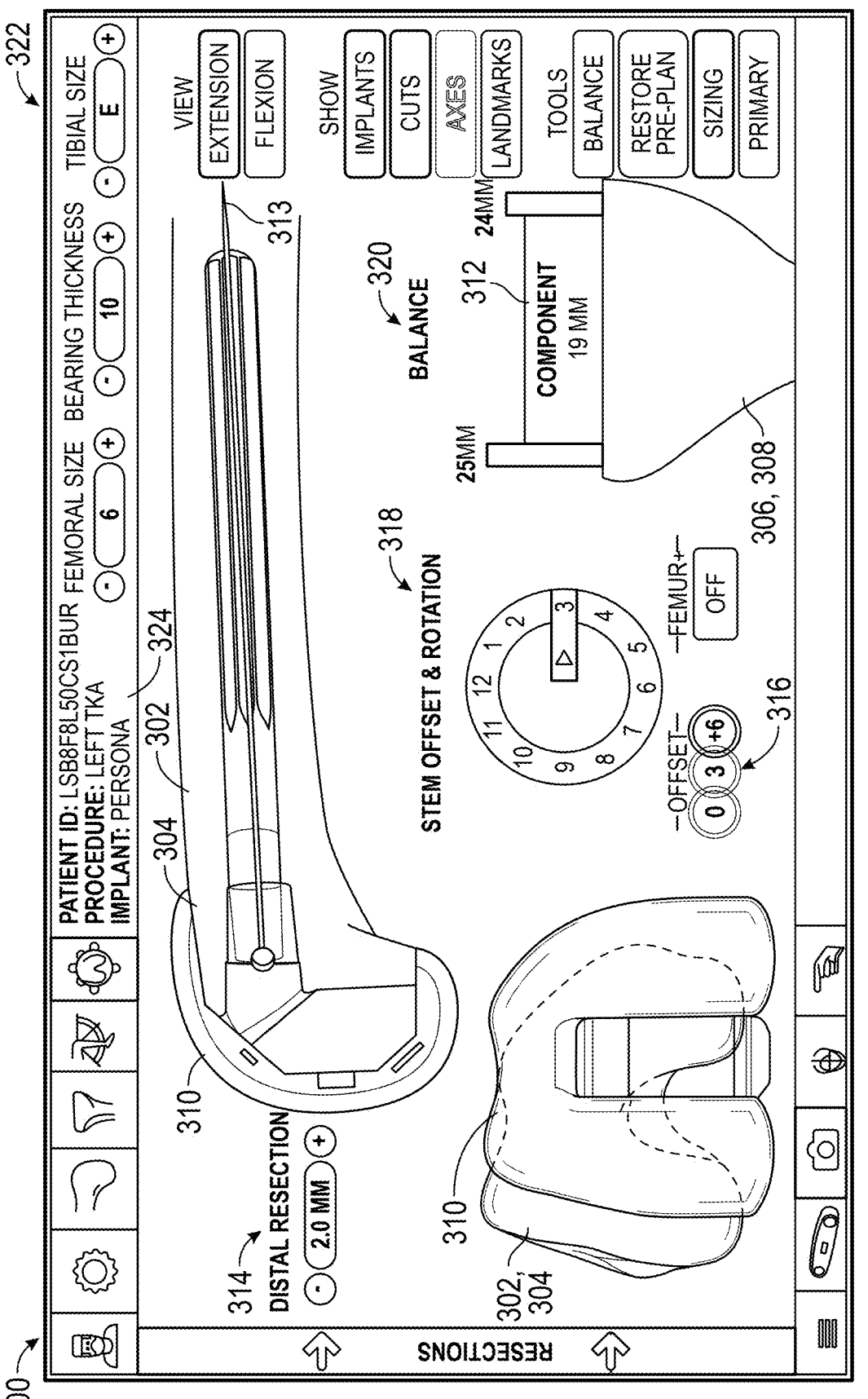
FIG. 5 illustrates an example of a user interface for planning aspects of the revision knee arthroplasty (e.g., resection, balance, stem offset, stem rotation, implant v. bone positioning display) in accordance with at least one example of this disclosure.

FIG. 5 illustrates a user interface 300 of a model for planning aspects of the revision knee arthroplasty (e.g., display of a virtual or mixed reality rendering of the bones of the patient, positioning of the new revision implants on the virtual rendering of the bones of the patient) in accordance with at least one example of this disclosure. For example, the user interface 300 may be used for new implant planning, new implant positioning, control of the robotic surgical system (e.g., 100 in FIG. 1), control of system components, or the like.

FIG. 5 shows a virtual rendering of a surface 302 of a femur 304 and a virtual rendering of a surface 306 of a tibia 308. Surfaces 302, 304 can be displayed semi-transparent for example. A femoral revision implant 310 is displayed with positioning relative to the femur 304. Similarly, a tibial implant 312 is displayed with positioning relative to the tibia 308. The implants 310, 312 can be semi-transparent in some cases to show the position of the implant 310 or 312 relative to the virtual rendering of the bone, for example. Anatomical data can optionally be displayed such as the axis 313 (mechanical and/or anatomic axis corresponding to the intramedullary canal). Various positioning criteria such as distal resection depth 314, an offset of the stem 316, a rotation of the stem 318, implant balance 320 are also displayed for reference. Similarly, criteria relating to implant size 322 and implant type 324 (e.g., brand) are also displayed. These various positioning criteria and implant related criteria can be adjusted by a user intraoperative or preoperatively. Such adjustment can lead to replanning and updated display with the selected criteria updated accordingly for review by the user. For example, based upon the position of the femoral revision implant 310 relative to the femur 304 the user would need to adjust the offset of the stem 316 from +6 mm to 0 mm. The model then would replan accordingly and redisplay with the 0 mm for the offset of the stem 316 implemented. According to some examples, the model could offer the user suggestions on positioning. Thus, a suggestion as in FIG. 5A to "Reposition the offset of the stem from +6 mm to 0 mm." could be displayed to the user.

FIG. 5B illustrates a warning that can be issued that "[b]ased upon your selection regarding one or more of the offset of the stem, the size of the stem or a size of a bone interfacing feature that cortex fracture may occur". Various other user prompts based upon user selections can be generated as contemplated herein. These can include to remind the user a step of the arthroplasty has been missed, confirm completion of each step of the arthroplasty, affirm selection of a final combination of implants made virtually by the user, or confirm that all bone preparation is complete and ready for use of trial implants or for the final combination of implants to be implanted on the bone, for example.

Figure 6:
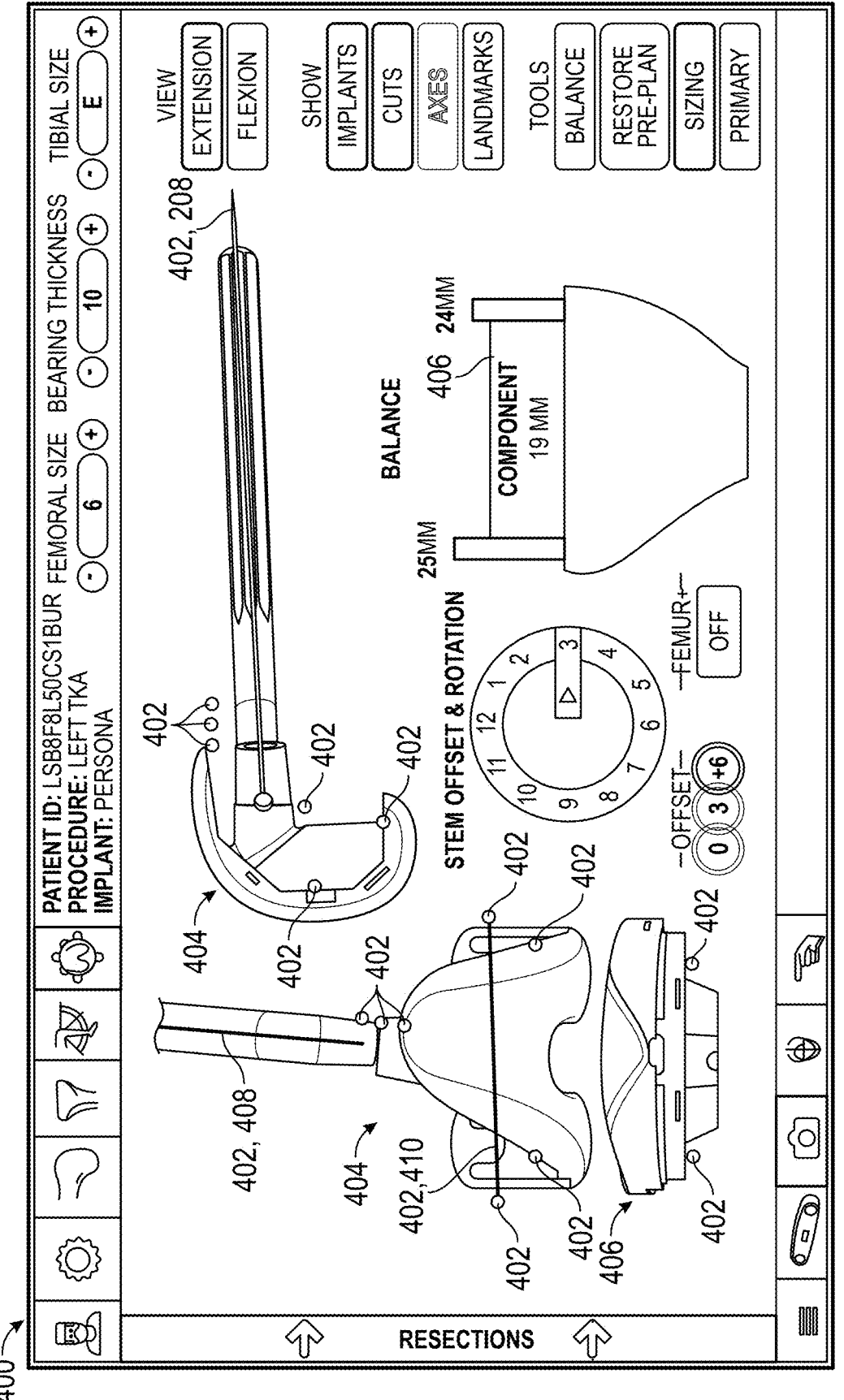
FIG. 6 illustrates another example of a user interface including a model with display of various landmarks and display of these landmarks relative to revision implants accordance with at least one example of this disclosure.

FIG. 6 illustrates a user interface 400 of a model for planning aspects of the revision knee arthroplasty (e.g., display of landmarks of the bones of the patient, positioning of the new revision implants relative to landmarks of the bones of the patient) in accordance with at least one example of this disclosure. The landmarks 402 can be displayed relative to a femoral revision implant 404 and/or a tibial revision implant assembly 406 (baseplate and/or poly). The landmarks 402 can be gathered using the registration and other techniques discussed previously and discussed in further detail subsequently in regards to FIGS. 10-12. The landmarks 402 can include the axis 408 (anatomic and/or mechanical approximated by the intramedullary canal). The axis 408 can be determined using the navigation techniques and devices discussed previously. Further of the landmarks 402 can include a trans-epicondylar axis 410 position and/or length, one or more points on the condyles or resected surfaces of the femur (e.g., posterior, distal), one or more points or axes along the sulcus or resected anterior surface of the femur (e.g., an anteroposterior axis, one or more points along the anterior cortex, etc.), one or more points along a medial portion of the tibia, one or more points along a lateral portion of the tibia, etc.

FIG. 6 illustrates the user interface 400 can have the various positioning criteria and implant related criteria which can be adjusted by a user intraoperative or preoperatively as discussed previously. These can result in replanning and redisplay as discussed of the implants 404, 406 relative to the landmarks 402.

Figure 7:
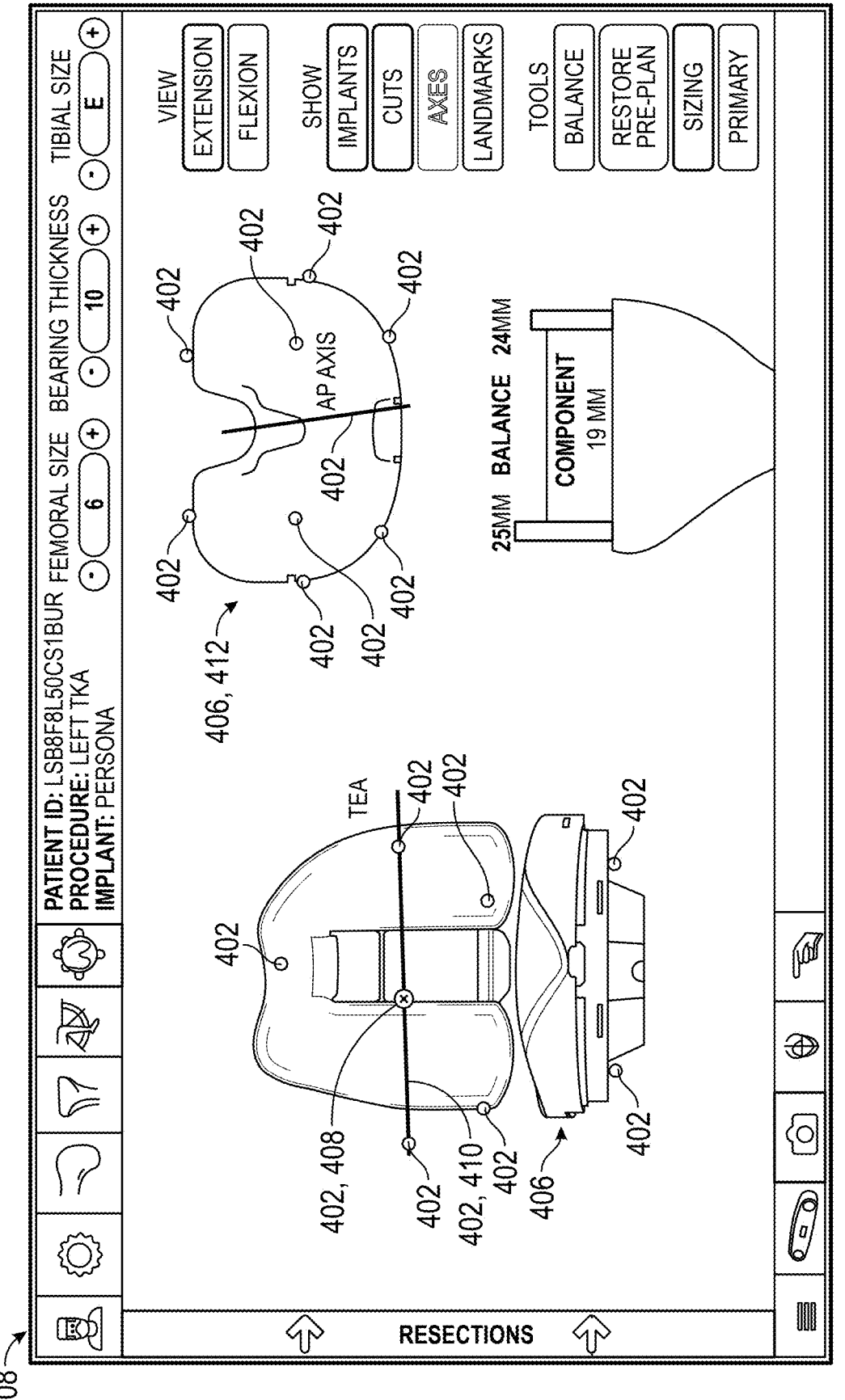
FIG. 7 illustrates the user interface of FIG. 6 with further landmarks displayed on the model and relative to further views of the revision implants.

FIG. 7 illustrates the user interface of FIG. 6 with further of the landmarks 402 displayed on the model and relative to further views of the revision implants 404, 406. For example, FIG. 7 shows a flexion view of the femoral implant 404 with the axis 408 displayed relative to the trans-epicondylar axis 410. FIG. 7 further illustrates a posterior of a baseplate 412 of the tibial revision implant assembly 406 with various additional of the landmarks 402 displayed.

Figure 8:
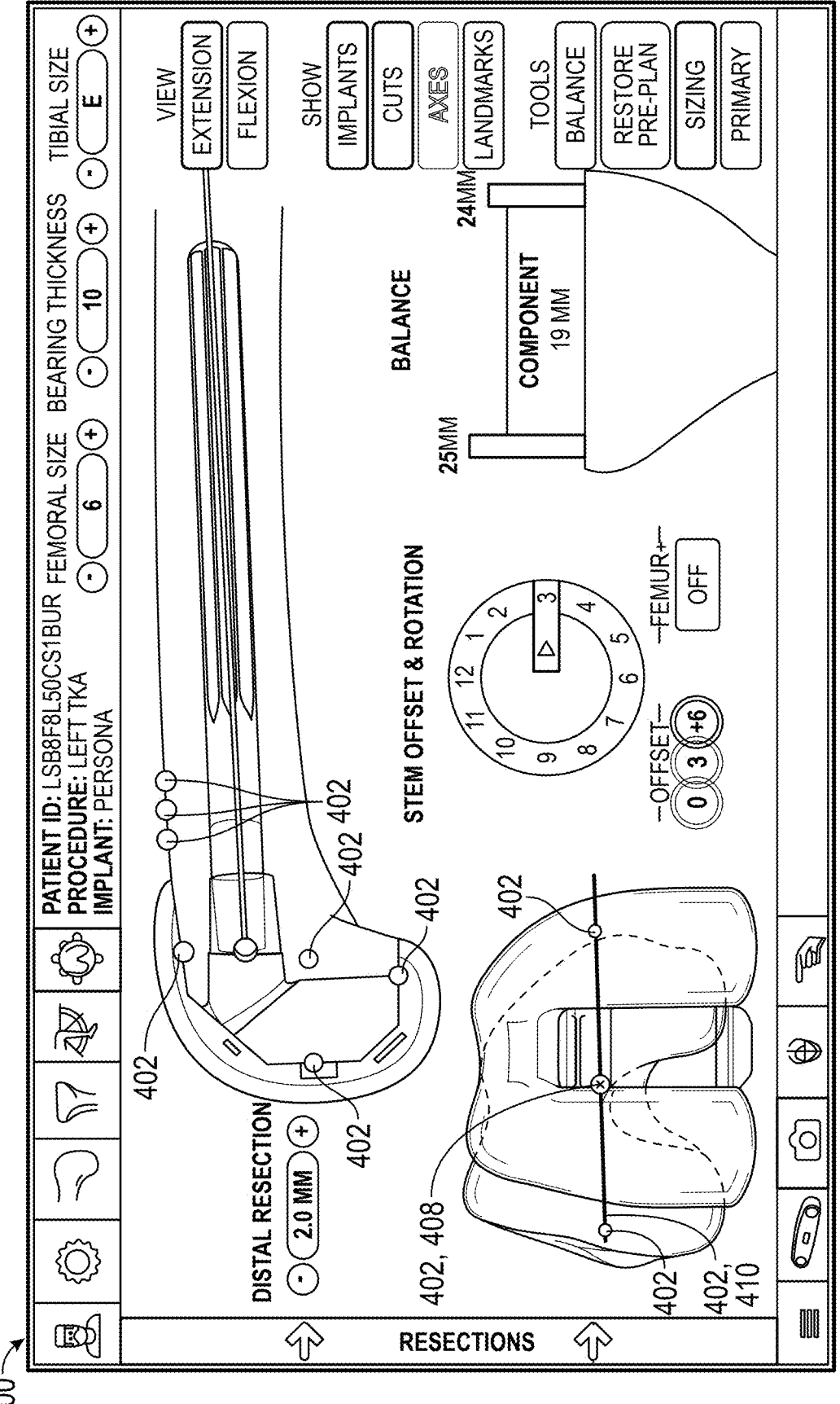
FIG. 8 illustrates an example of a user interface for planning aspects of the revision knee arthroplasty with the model displaying surfaces of relevant bones, landmarks of the relevant bones, illustrating implants and the implants positioning based upon user selection relative to the bones and landmarks in accordance with at least one example of this disclosure.

FIG. 8 a user interface 500 of a model for planning aspects of the revision knee arthroplasty (e.g., display of landmarks overlayed on surfaces of the bones of the patient, positioning of the new revision implants relative to landmarks and on surfaces of the bones of the patient) in accordance with at least one example of this disclosure. The model of FIG. 8 combines aspects of the examples of FIGS. 5-7 for further functionality.

Figure 9:
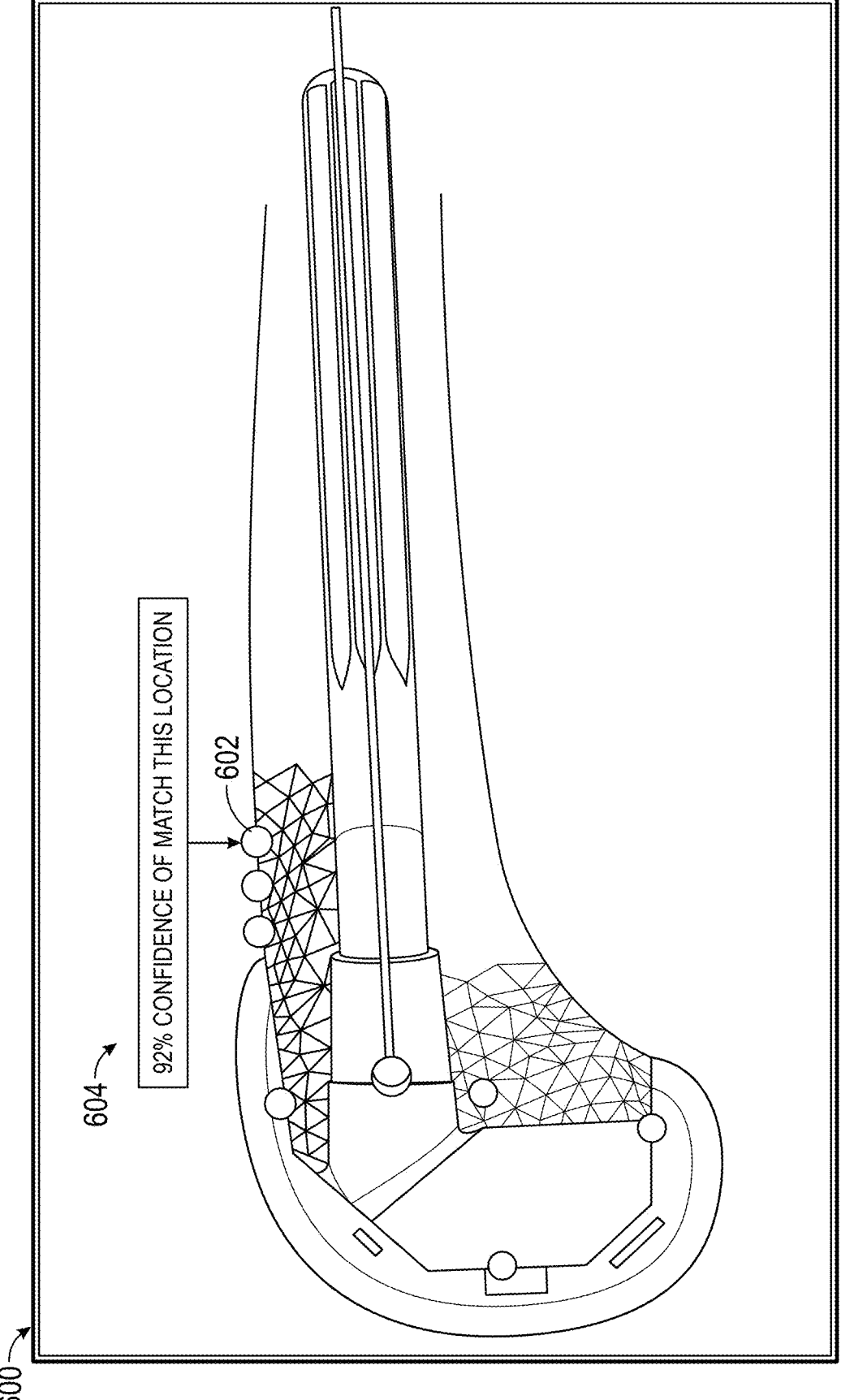
FIG. 9 illustrates an example of a user interface for planning aspects of the revision knee arthroplasty with landmarks displayed on the model and providing an indication of a confidence in a match between the landmarks and the model in accordance with at least one example of this disclosure.

FIG. 9 shows another user interface 600 such as one on a mixed reality device. The user interface 600 shows a model for planning aspects of the revision knee arthroplasty wherein the model includes the display of landmarks 602 on the model but these are also provided an indication of a confidence 604 in a match between one or more of the landmarks and the model. The landmarks 602 or confidence 604 can be semi-transparent and/or color coded. The user can click on a particular one of the landmarks 602 or area near the landmark and a confidence score in the model matching the actual bone at that landmark can be displayed, for example. Areas on the model of higher confidence can be visually indicated to the user through highlighted areas, screen prompts or popups, areas of brighter visibility relative to other areas or other indicia.

Figure 10:
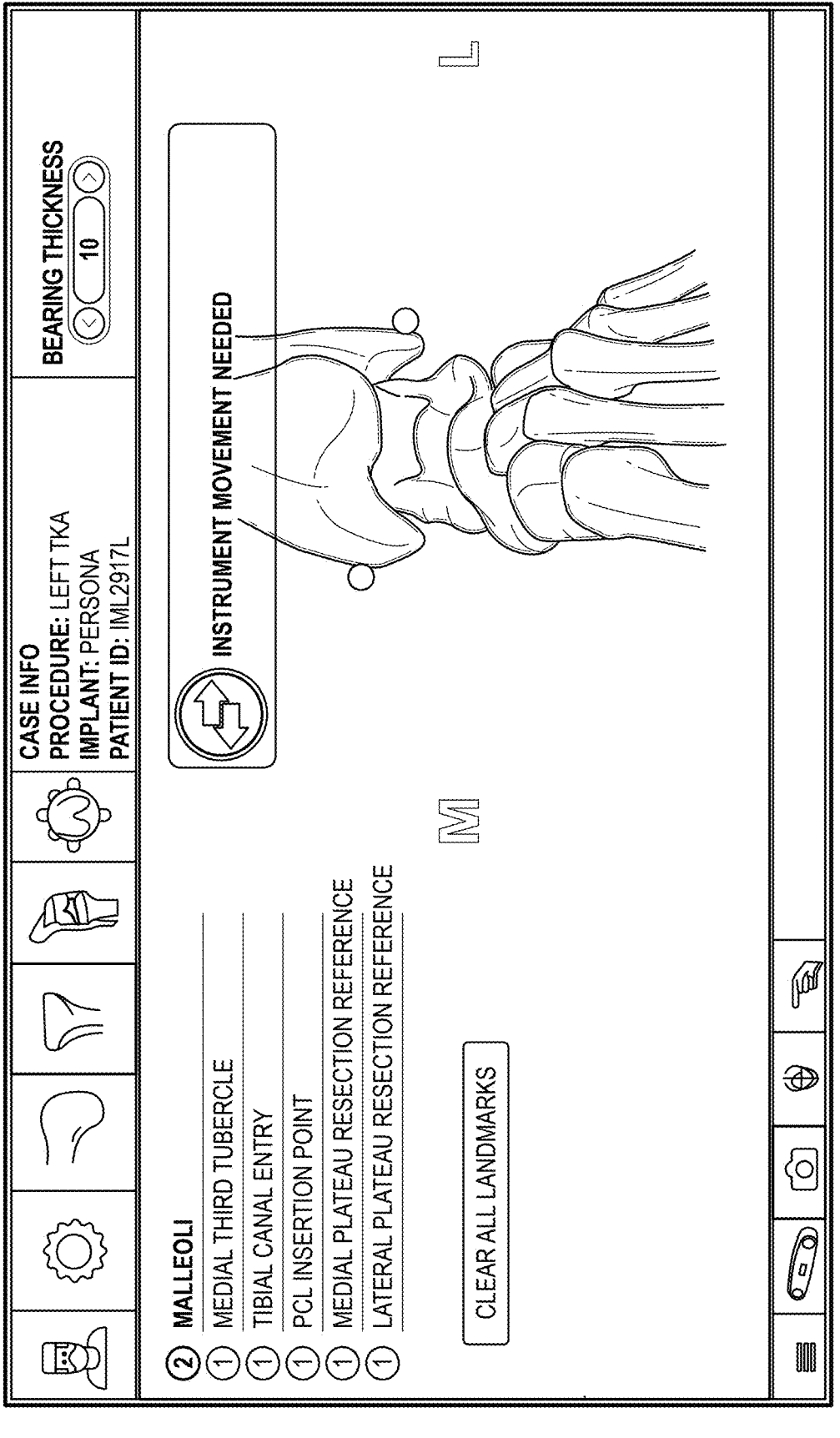
FIGS. 10-12 show a user interface of the robotic surgical system for gathering various landmarks of the ankle, hip and knee, the various landmarks can be gathered using the robotic surgical system in accordance with at least one example of this disclosure.
Figure 11:
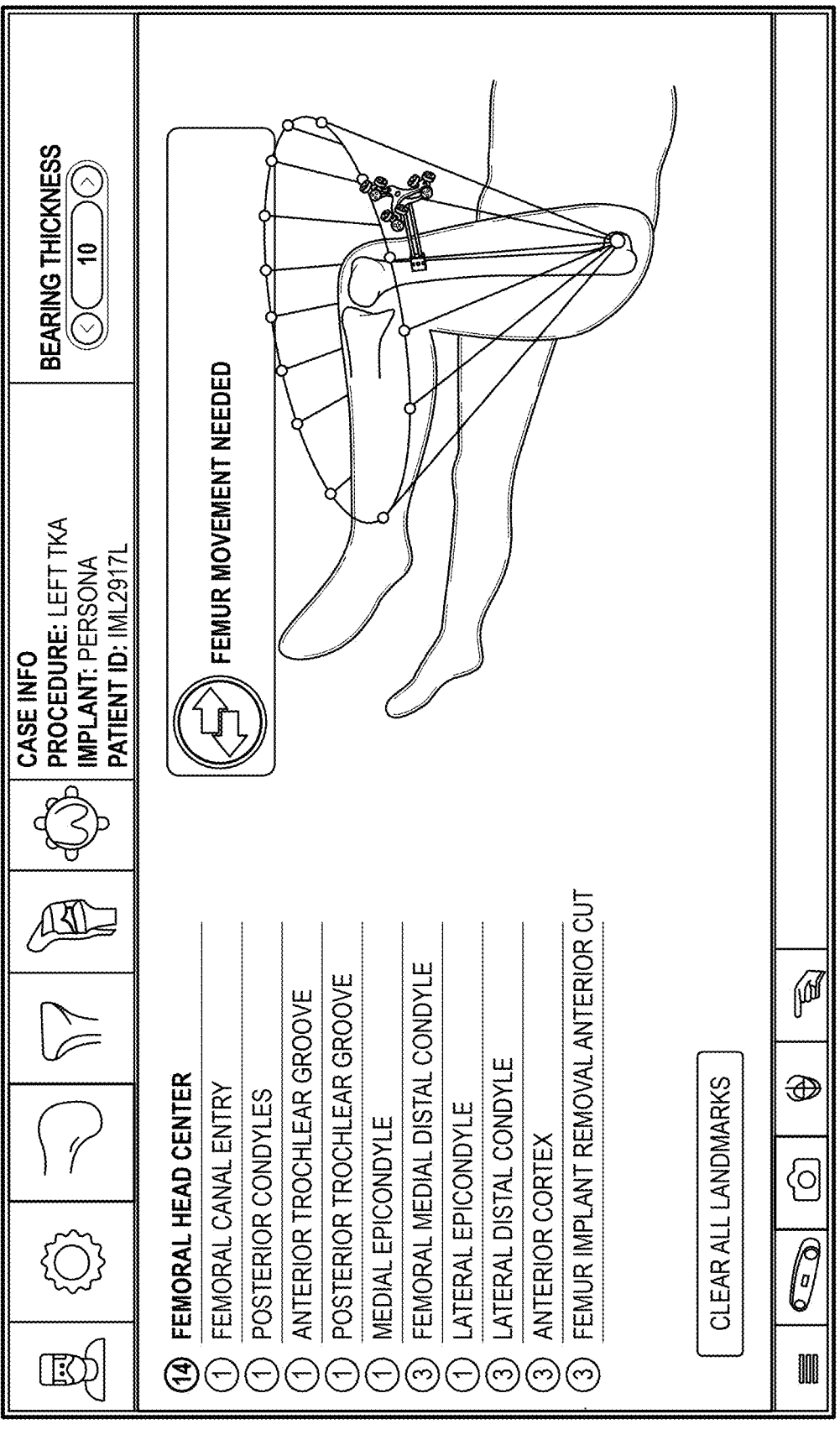
Figure 12:
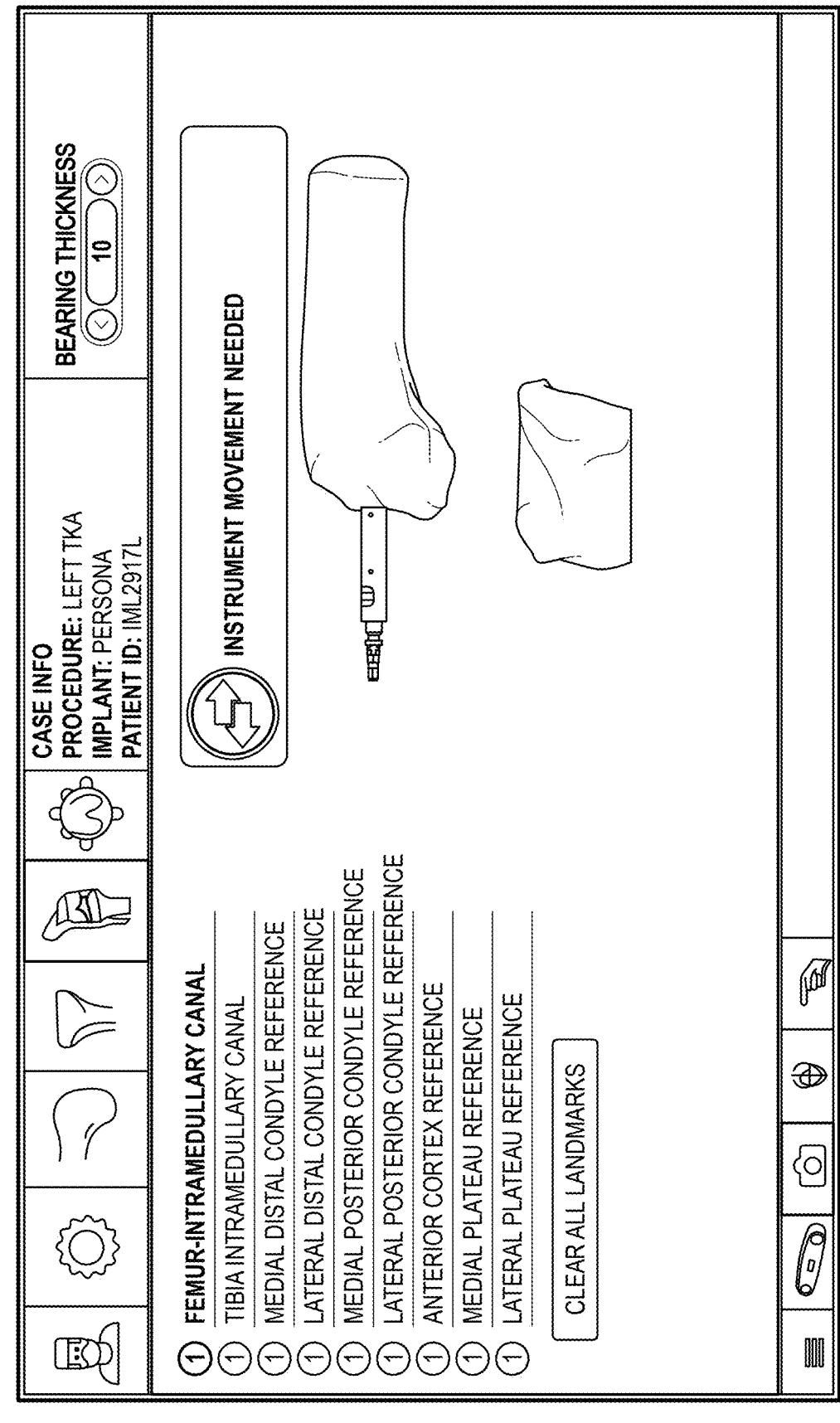

FIGS. 10-12 show various reference points that can be gathered using a robotic surgical system such as the robotic surgical system 100 of FIG. 1 to register one or more bones of the patient. In this manner, the one or more bones can be digitized. The robotic arm 102 can manipulate an instrument such as a pointer, probe, or navigation device such as those previously discussed in this registration process. Some or all of the registration points gathered during this process can be displayed to the user via a user interface as shown in FIGS. 10-12. The user interface can include prompts for user input and/or user guided feedback to the robotic surgical system.

FIG. 10 shows reference points 700 being gathered from an ankle of the patient. FIG. 11 shows reference points 702 being gathered about the hip of the patient. FIG. 12 shows reference points 704 being gathered from the knee joint of the patient. The reference points gathered in FIGS. 10-12 can become anatomical data such as landmarks that can be used for the generation of one or more of the models as previously discussed herein.

FIG. 13 shows exemplary factors (demographic and anatomical) that can be used to generate the updated model discussed in reference to FIG. 1. Optionally, these factors can be used to modify the mean bone model as discussed or to select an appropriate mean bone model from the modeling system as discussed in FIG. 1. The factors shown are purely exemplary and other further criteria can be utilized according to further examples. These factors include the gender of the patient, the length of the axis (mechanical and/or anatomic), the length of the trans-epicondylar axis, the axis angle (mechanical axis angle and/or anatomical axis angle) as determined in a sagittal plane and the axis angle (mechanical axis angle and/or anatomical axis angle) as measured in a frontal plane.

FIG. 14A shows a bone model 800 displayed in conjunction with an image 802 of the tibia of the patient in accordance with at least one example of this disclosure. Such display of FIGS. 14A and 14B can be on a mixed reality device, for example. Similarly, FIG. 14B shows a bone model 900 displayed in conjunction with an image 902 of the femur of the patient in accordance with at least one example of this disclosure. The images 802, 902 can be generated using known imaging modality such as CT, MRI, X-ray, etc. Areas of correspondence or that lack correspondence between the bone models 800, 900 and the bone as rendered in the images 802, 902 can be displayed for reference by the user. These areas of correspondence or lack of correspondence can be highlighted by color difference between the model and the bone and/or visual indicators (e.g. ellipses, arrows, etc.) The bone models 800, 900 can be semi-transparent allowing the images 802, 902 to be visualized through the bone models 800, 900 by overlay. Machine learning and other computer implements techniques can be implanted to better understand and reduce instances where there is a lack of correspondence between the bone models 800, 900 and the bone as rendered in the images 802, 902.

Figure 15:
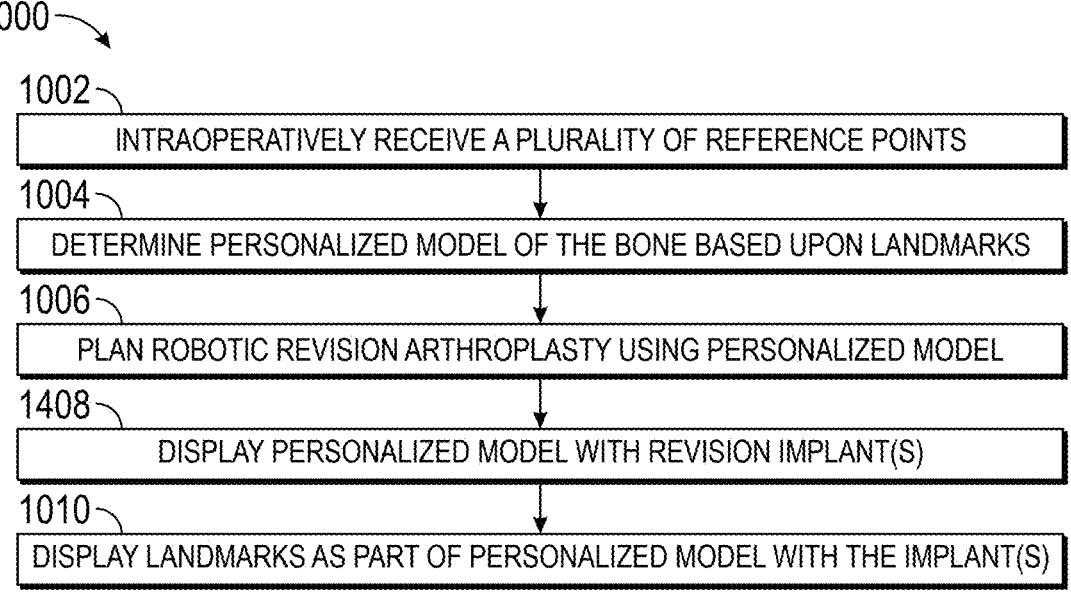
FIG. 15 illustrates a flowchart showing a technique for performing a robotic revision knee arthroplasty in accordance with at least one example of this disclosure.

FIG. 15 illustrates a flowchart illustrating a technique 1000 for performing a robotic revision knee arthroplasty in accordance with some embodiments. The technique 1000 includes an operation 1002 to intraoperatively receive a plurality of reference points after a primary implant has been removed from a bone. The plurality of reference points can correspond to a plurality of landmarks of the bone of a patient. The plurality of landmarks can include a position of an intramedullary canal of the bone.

The technique 1000 includes an operation 1004 using a processor to determine a personalized model comprising a best fit to an anatomy of the bone of the patient based upon the plurality of landmarks. The technique 1000 includes an operation 1006 to plan the robotic revision knee arthroplasty using the personalized model. In an example, operation 1006 includes display 1008 of the personalized model with one or more revision implants and display 1010 of the plurality of landmarks as part of the personalized model with the one or more revision implants.

The technique 1000 includes various other operations to replan for a new implant to be affixed to the bone of the knee. In an example, operation includes using predictive analytics or a bone model selection, user prompt, or the like to replan for the new implant. The technique may include an operation to install the new implant, for example using the robotic surgical device as a guide, using the robotic surgical device to move the implant, using the robotic surgical device as a force-assist device, or the like.

The technique 1000 may include an operation to use optical navigation, probe, pointer, etc. to register the reference points. The technique may include an operation to robotically prepare a bone canal for the new implant. The technique may include an operation to plan and perform bone resection, plan a clean-up cut after the (initial) resection is performed, etc.

Figure 16:
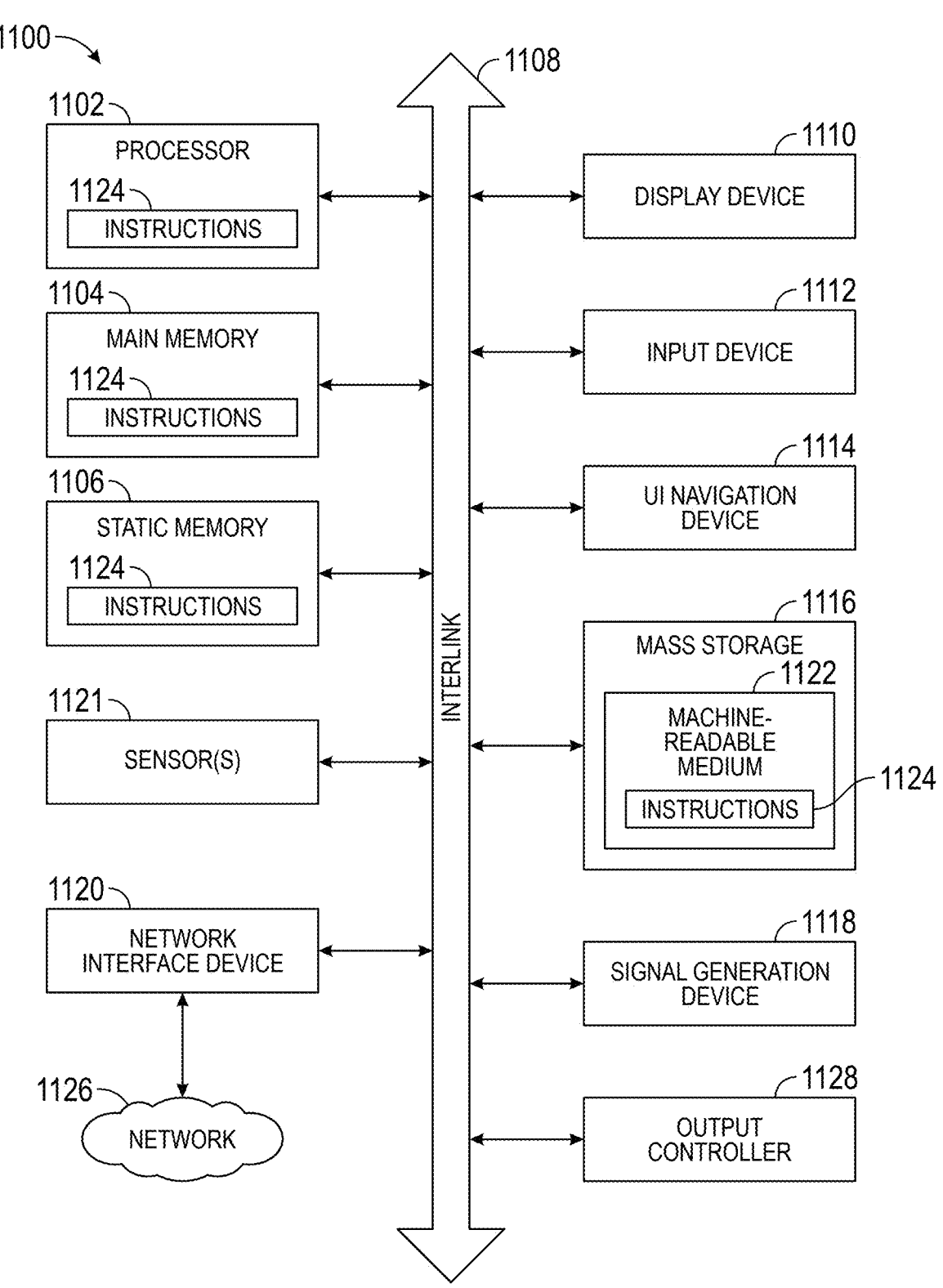
FIG. 16 illustrates a block diagram of an example machine upon which any one or more of the techniques discussed herein may perform in accordance with at least one example of this disclosure.

FIG. 16 illustrates a block diagram of an example machine 1100 upon which any one or more of the techniques discussed herein may perform in accordance with some embodiments. In alternative embodiments, the machine 1100 may operate as a standalone device or may be connected (e.g., networked) to other machines. In a networked deployment, the machine 1100 may operate in the capacity of a server machine, a client machine, or both in server-client network environments. In an example, the machine 1100 may act as a peer machine in peer-to-peer (P2P) (or other distributed) network environment. The machine 1100 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1100 may include a hardware processor 1102 (e.g., a central processing unit (CPU), a graphics processing unit (GPU), a hardware processor core, or any combination thereof), a main memory 1104 and a static memory 1106, some or all of which may communicate with each other via an interlink (e.g., bus) 1108. The machine 1100 may further include a display unit 1110, an alphanumeric input device 1112 (e.g., a keyboard), and a user interface (UI) navigation device 1114 (e.g., a mouse). In an example, the display unit 1110, input device 1112 and UI navigation device 1114 may be a touch screen display. The machine 1100 may additionally include a storage device (e.g., drive unit) 1116, a signal generation device 1118 (e.g., a speaker), a network interface device 1120, and one or more sensors 1121, such as a global positioning system (GPS) sensor, compass, accelerometer, or other sensor. The machine 1100 may include an output controller 1128, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 1116 may include a machine readable medium 1122 on which is stored one or more sets of data structures or instructions 1124 (e.g., software) embodying or utilized by any one or more of the techniques or functions described herein. The instructions 1124 may also reside, completely or at least partially, within the main memory 1104, within static memory 1106, or within the hardware processor 1102 during execution thereof by the machine 1100. In an example, one or any combination of the hardware processor 1102, the main memory 1104, the static memory 1106, or the storage device 1116 may constitute machine readable media.

While the machine readable medium 1122 is illustrated as a single medium, the term "machine readable medium" may include a single medium or multiple media (e.g., a centralized or distributed database, and/or associated caches and servers) configured to store the one or more instructions 1124. The term "machine readable medium" may include any medium that is capable of storing, encoding, or carrying instructions for execution by the machine 1100 and that cause the machine 1100 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 1124 may further be transmitted or received over a communications network 1126 using a transmission medium via the network interface device 1120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1120 may include one or more physical jacks (e.g., Ethernet, coaxial, or phone jacks) or one or more antennas to connect to the communications network 1126. In an example, the network interface device 1120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1100, and includes digital or analog communications signals or other intangible medium to facilitate communication of such software.

Figure 17:
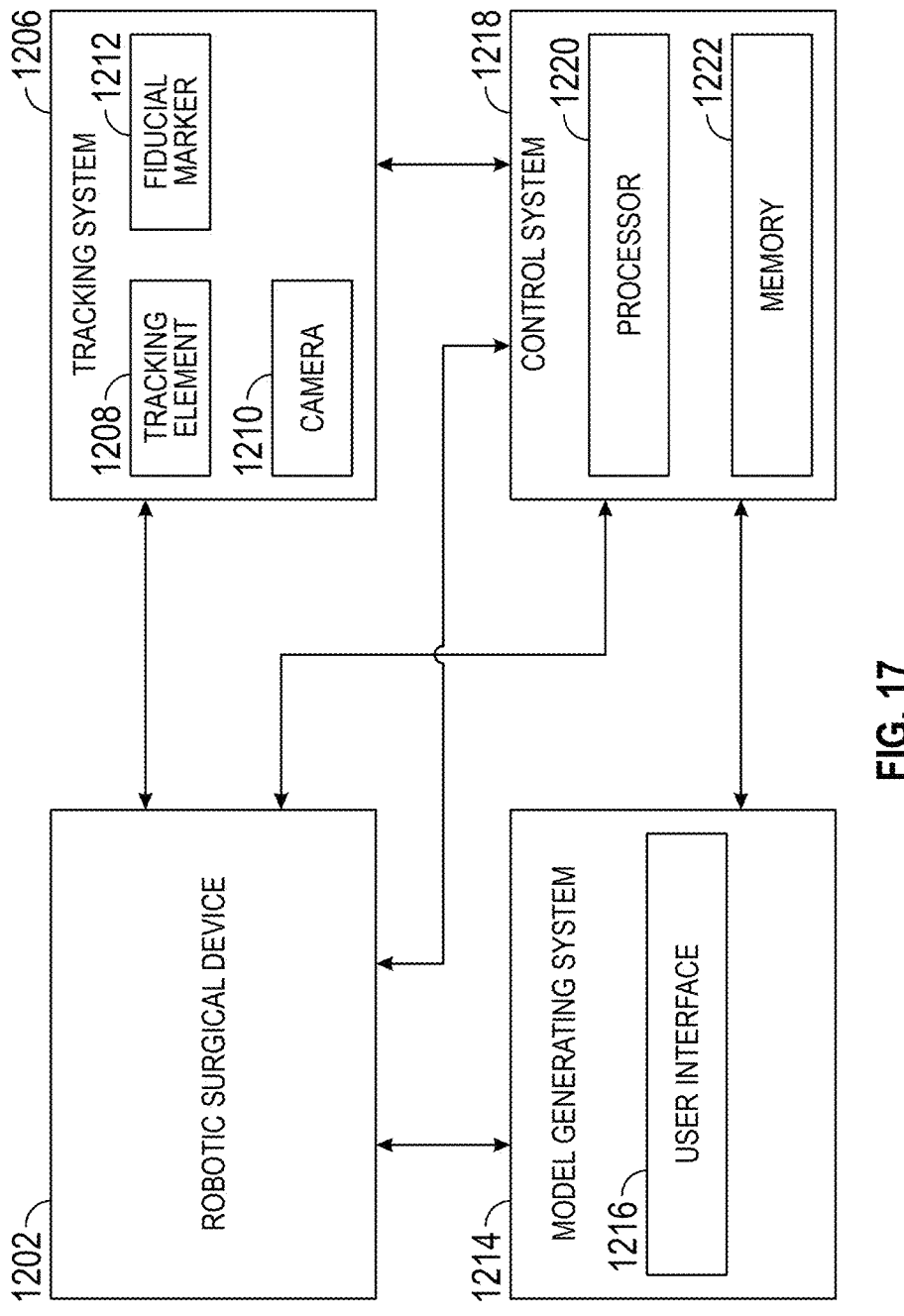
FIG. 17 is a schematic illustration of a robotic surgical system incorporating a navigation tool assembly of the present application interacting with a tracking system in accordance with at least one example of this disclosure.

FIG. 17 illustrates a robotic surgical system 1200 for performing techniques described herein, in accordance with some embodiments. System 1200 can include a robotic surgical device 1202 (such as an arm), which may interact with tracking system 1206, control system 1218 and model generating system 1214. The tracking system 1206 can include tracking element 1008, camera 1210 and fiducial marker or other indicia 1212. The robotic surgical system 1200 can include the model generating system 1214, which can be displayed and interacted with on a user interface 1016. The model generating system 1214 can include various inputs, criteria, resources (e.g., mean models), planning and implementation aspects as discussed previously. The robotic surgical system 1200 can include the control system 1218 (e.g., a robotic controller), including processor 1220 and memory 1222. In an example, model generating system 1214 can be communicatively coupled to one or more of robotic surgical device 1202, the tracking system 1206, or the control system 1218.

Each of the following non-limiting examples may stand on its own, or may be combined in various permutations or combinations with one or more of the other examples.

Example 1 is a system for performing a robotic revision knee arthroplasty, the system optionally comprising any one or combination of: a robotic surgical device; a user interface having a display; and processor, communicatively coupled to the surgical robotic device and the user interface. The processor can optionally be configured to: intraoperatively receive a plurality of position data obtained by the robotic surgical device after a primary implant has been removed from a bone, wherein the plurality of position data correspond to a plurality of landmarks of the bone of a patient, wherein the plurality of landmarks include a position of an intramedullary canal of the bone: select from a database having a plurality of mean models of a corresponding bone a mean model that comprises a best match based upon the plurality of landmarks of the bone; generate an updated model by altering the mean model to fit an anatomy of the bone of the patient based upon the plurality of landmarks; and output to the user interface the updated model for use during the robotic revision knee arthroplasty.

Example 2 is the system of Example 1, wherein optionally the updated model virtually replicates in at least two dimensions the bone of the patient.

Example 3 is the system of Example 2, wherein optionally the processor is configured to generate virtual representations of one or more revision implants and is configured to superimpose the one or more revision implants on the updated model including on the virtual replication of the bone of the patient.

Example 4 is the system of Example 3, wherein optionally the updated model shows the plurality of landmarks as one or more of points, at least one axis or a combination of one or more points and at least one axis, and wherein the one or more of points, the at least one axis or the combination of one or more points and at least one axis are reproduced on the bone model of the patient.

Example 5 is the system of Example 1, wherein optionally the updated model shows the plurality of landmarks as one or more of points, at least one axis or a combination of one or more points and at least one axis.

Example 6 is the system of Example 5, wherein optionally the processor is configured to generate virtual representations of one or more revision implants and is configured to superimpose the plurality of landmarks as the one or more of points, the at least one axis or the combination of the one or more points and the at least one axis on the one or more revision implants.

Example 7 is the system any one of Examples 1-6, wherein the updated model shows a degree of confidence of the updated model matching the anatomy of the bone of the patient at the plurality of landmarks.

Example 8 is the system of any one of Examples 1-7, wherein optionally the processor is configured to generate virtual representations of one or more an offset of a stem, a rotation of the stem, a brand of revision implant, a size of the revision implant, a reproduction of a knee joint line of the patient, and one or more resections to the bone, and wherein one or more of these virtual representations are displayed with the updated model.

Example 9 is the system of Example 8, wherein optionally the processor is configured via input from the user interface to: alter the virtual representations to reflect changes by the user to one or more of the offset of the stem, the rotation of the stem, the brand of the revision implant, the size of the revision implant, the reproduction of a knee joint line of the patient, and the one or more resections to the bone, and wherein one or more of these altered virtual representations are displayed with the updated model.

Example 10 is the system of any one of Examples 8-9, wherein optionally the processor is configured via the user interface to issue a warning that based upon a virtual selection by the user regarding one or more of the offset of the stem, the size of the stem or a size of a bone interfacing feature that a breakage of the bone is likely to occur if such selection is implemented during the arthroplasty.

Example 11 is the system of any one of Examples 1-10, wherein optionally the processor is configured via the user interface to prompt the user to one or more of: remind the user a step of the arthroplasty has been missed, confirm completion of each step of the arthroplasty, affirm selection of a final combination of implants made virtually by the user, or confirm that all bone preparation is complete and ready for use of trial implants or for the final combination of implants to be implanted on the bone.

Example 12 is the system of any one of Examples 1-11, wherein optionally the processor is configured to overlay an image of the bone on the updated model, wherein the image is derived from imaging the bone of the patient.

Example 13 is the system of Example 12, wherein optionally the overlay is displayed on a mixed reality device.

Example 14 is the system of any one of Examples 12 or 13, wherein optionally one of the image of the bone or the updated model is displayed semi-transparent.

Example 15 is the system of any one of Examples 12-14, wherein optionally areas of correspondence or lack of correspondence between the image of the bone and the updated model are highlighted by at least one of a color difference or indicia.

Example 16 is the system of any one of Examples 1-15, further optionally comprising a navigation tool configured to couple to a reamer, wherein the processor, based upon a position of the navigation tool when mounted to the reamer, determines the position of the intramedullary canal of the bone.

Example 17 is the system of Example 16, wherein optionally the processor is configured to intraoperatively register the intramedullary canal of the bone using the navigation tool for the arthroplasty.

Example 18 is a system for performing a robotic revision knee arthroplasty, the system can optionally include any one or combination of: a reamer; a navigation tool configured to couple to the reamer; and a robotic surgical device. The robotic surgical device can include any one or combination of a processor configured to: intraoperatively receive position data regarding a position of the navigation tool when coupled to the reamer after a primary implant has been removed from a bone of a patient, determine based upon the position data a position of an intramedullary canal of the bone based upon the position of the navigation tool, and output to a user interface for display the position of the intramedullary canal for use during the robotic revision knee arthroplasty.

Example 19 is the system of Example 18, wherein optionally the processor is configured to based upon the determined position of the intramedullary canal: select from a database having a plurality of mean models of a corresponding bone a mean model that comprises a best match based upon at least the position of the intramedullary canal; generate an updated model by altering the mean model to fit an anatomy of the bone of the patient based upon at least the position of the intramedullary canal; and output to the user interface for display the updated model for use during the robotic revision knee arthroplasty.

Example 20 is the system of Example 18, wherein optionally the updated model shows the position of the intramedullary canal as an axis on the updated model.

Example 21 is the system of Example 18, wherein optionally the updated model virtually replicates in at least two dimensions the bone of the patient.

Example 22 is the system of Example 21, wherein optionally the processor is configured to generate virtual representations of one or more revision implants and is configured to superimpose the one or more revision implants on the updated model including on the virtual replication of the bone of the patient.

Example 23 is the system of Example 22, wherein optionally the updated model shows a plurality of landmarks including the intramedullary canal as a combination of one or more points and at least one axis, and wherein the combination of one or more points and at least one axis are reproduced on the bone model of the patient.

Example 24 is the system of Example 18, wherein optionally the updated model shows a plurality of landmarks including the intramedullary canal as a combination of one or more points and at least one axis.

Example 25 is the system of Example 24, wherein optionally the processor is configured to generate virtual representations of one or more revision implants and is configured to superimpose the plurality of landmarks as the combination of the one or more points and the at least one axis on the one or more revision implants.

Example 26 is the system any one of Examples 1-25, wherein optionally the updated model shows a degree of confidence of the updated model matching the anatomy of the bone of the patient at the plurality of landmarks.

Example 27 is the system of any one of Examples 18-26, wherein optionally the processor is configured to generate virtual representations of one or more an offset of a stem, a rotation of the stem, a brand of revision implant, a size of the revision implant, a reproduction of a knee joint line of the patient, and one or more resections to the bone, and wherein one or more of these virtual representations are displayed with the updated model.

Example 28 is the system of Example 27, wherein optionally the processor is configured via input from the user interface to: alter the virtual representations to reflect changes by the user to one or more of the offset of the stem, the rotation of the stem, the brand of the revision implant, the size of the revision implant, the reproduction of a knee joint line of the patient, and the one or more resections to the bone, and wherein one or more of these altered virtual representations are displayed with the updated model.

Example 29 is the system of any one of Examples 27-28, wherein optionally the processor is configured via the user interface to issue a warning that based upon a virtual selection by the user regarding one or more of the offset of the stem, the size of the stem or a size of a bone interfacing feature that a breakage of the bone is likely to occur if such selection is implemented during the arthroplasty.

Example 30 is the system of any one of Examples 18-29, wherein optionally the processor is configured via the user interface to prompt the user to one or more of: remind the user a step of the arthroplasty has been missed, confirm completion of each step of the arthroplasty, affirm selection of a final combination of implants made virtually by the user, or confirm that all bone preparation is complete and ready for use of trial implants or for the final combination of implants to be implanted on the bone.

Example 31 is the system of any one of Examples 19-30, wherein optionally the processor is configured to overlay an image of the bone on the updated model, wherein the image is derived from imaging the bone of the patient.

Example 32 is the system of any one of Examples 18-31, wherein optionally the processor is configured to intraoperatively register the intramedullary canal of the bone using the navigation tool for the arthroplasty.

Example 33 is a method of performing a robotic revision knee arthroplasty, the method can optionally include any one or combination of: intraoperatively receiving a plurality of reference points after a primary implant has been removed from a bone, wherein the plurality of reference points correspond to a plurality of landmarks of the bone of a patient, wherein the plurality of landmarks include a position of an intramedullary canal of the bone; using a processor, determining a personalized model comprising a best to fit an anatomy of the bone of the patient based upon the plurality of landmarks; and planning the robotic revision knee arthroplasty using the personalized model. The planning can include any one or combination of: displaying the personalized model with one or more revision implants, and displaying the plurality of landmarks as part of the personalized model with the one or more revision implants.

Example 34 is the method of Example 33, wherein optionally planning the robotic revision knee arthroplasty using the personalized model includes shifting one of an offset of a stem or a rotation of the stem of the one or more revision implants.

Example 35 is the method of any one of Examples 33-34, wherein optionally the personalized model virtually replicates in at least two dimensions the bone of the patient.

Example 36 is the method of Example 35, wherein optionally displaying the personalized model with the one or more revision implants includes superimposing the one or more revision implants on the personalized model including on the virtual replication of the bone of the patient.

Example 37 is the method of Example 36, wherein optionally displaying the plurality of landmarks as part of the personalized model with the one or more revision implants shows the plurality of landmarks as one or more of points, at least one axis or a combination of one or more points and at least one axis, and wherein the one or more of points, the at least one axis or the combination of one or more points and at least one axis are reproduced on the personalized model of the patient.

Example 38 is the method of any one of Examples 33-34, wherein optionally displaying the plurality of landmarks as part of the personalized model with the one or more revision implants shows the plurality of landmarks as one or more of points, at least one axis or a combination of one or more points and at least one axis.

Example 39 is the method of Example 38, wherein optionally displaying the plurality of landmarks as part of the personalized model with the one or more revision implants includes superimposing the plurality of landmarks as the one or more of points, the at least one axis or the combination of the one or more points and the at least one axis on the one or more revision implants.

Example 40 is the method any one of Examples 33-39, further optionally comprising displaying a degree of confidence of the personalized model matching the anatomy of the bone of the patient at the plurality of landmarks.

Example 41 is the method of Example 33, wherein optionally displaying the personalized model with one or more revision implants includes displaying virtual representations of one or more an offset of a stem, a rotation of the stem, a brand of revision implant, a size of the revision implant, a reproduction of a knee joint line of the patient, and one or more resections to the bone.

Example 42 is the method of Example 41, further optionally comprising altering the virtual representations to reflect changes by a user to one or more of the offset of the stem, the rotation of the stem, the brand of the revision implant, the size of the revision implant, the reproduction of a knee joint line of the patient, and the one or more resections to the bone, and displaying the one or more of these altered virtual representations with an updated model.

Example 43 is the method of any one of Examples 41-42, further optionally comprising outputting a warning that based upon a virtual selection by a user regarding one or more of the offset of the stem, the size of the stem or a size of a bone interfacing feature that a breakage of the bone is likely to occur if such selection is implemented during the arthroplasty.

Example 44 is the method of any one of Examples 33-43, further optionally comprising prompting the user to one or more of: remind the user a step of the arthroplasty has been missed, confirm completion of each step of the arthroplasty, affirm selection of a final combination of implants made virtually by the user, or confirm that all bone preparation is complete and ready for use of trial implants or for the final combination of implants to be implanted on the bone.

Example 45 is the method of any one of Examples 33-44, further optionally comprising: imaging the bone of the patient; and overlaying an image of the bone on an updated model.

Example 46 is the method of any one of Examples 33-45, further optionally comprising: coupling a navigation tool configured to a reamer; and determining with the computer, based upon a position of the navigation tool when mounted to the reamer, the position of the intramedullary canal of the bone.

Example 47 is the method of Example 46, further optionally comprising intraoperatively registering the intramedullary canal of the bone using the navigation tool for the arthroplasty.

Example 48 is a system to implement of any of Examples 1-47.

Example 49 is a method to implement of any of Examples 1-47.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system for performing a robotic revision knee arthroplasty, the system comprising:

a robotic surgical device;

a user interface having a display; and a processor, communicatively coupled to the surgical robotic device and the user interface, the processor configured to:

intraoperatively receive a plurality of position data obtained by the robotic surgical device after a primary implant has been removed from a bone, wherein the plurality of position data correspond to a plurality of landmarks of the bone of a patient, wherein the plurality of landmarks include a position of an intramedullary canal of the bone;

select from a database having a plurality of mean models of a corresponding bone a mean model that comprises a best match based upon the plurality of landmarks of the bone;

generate an updated model by altering the mean model to fit an anatomy of the bone of the patient based upon the plurality of landmarks;

generate a virtual replication of the bone of the patient based upon the updated model;

generate virtual representations of one or more revision implants;

superimpose the one or more revision implants on the updated model including on the virtual replication of the bone of the patient;

superimpose the plurality of landmarks as one or more of points, at least one axis or a combination of the one or more points and the at least one axis on the virtual replication of the bone of the patient and on the one or more revision implants;

output to the user interface the updated model with the virtual replication of the bone, the one or more revision implants, and the plurality of landmarks for use during the robotic revision knee arthroplasty; and controlling the robotic surgical device to perform the robotic revision knee arthroplasty based upon the undated model.

2. The system of claim 1, wherein the updated model virtually replicates in at least two dimensions the bone of the patient.

3. The system of claim 1, wherein the updated model shows a degree of confidence of the updated model matching the anatomy of the bone of the patient at the plurality of landmarks.

4. The system of claim 1, wherein the processor is configured to generate virtual representations of one or more an offset of a stem, a rotation of the stem, a brand of revision implant, a size of the revision implant, a reproduction of a knee joint line of the patient, and one or more resections to the bone, and wherein one or more of these virtual representations are displayed with the updated model.

5. The system of claim 4, wherein the processor is configured via input from the user interface to:
  alter the virtual representations to reflect changes by a user to one or more of the offset of the stem, the rotation of the stem, the brand of the revision implant, the size of the revision implant, the reproduction of a knee joint line of the patient, and the one or more resections to the bone, and wherein one or more of these altered virtual representations are displayed with the updated model.

6. The system of claim 4, wherein the processor is configured via the user interface to issue a warning that based upon a virtual selection by a user regarding one or more of the offset of the stem, the size of the stem or a size of a bone interfacing feature that a breakage of the bone is likely to occur if such selection is implemented during the arthroplasty.

7. The system of claim 1, wherein the processor is configured via the user interface to prompt a user to one or more of: remind the user a step of the arthroplasty has been missed, confirm completion of each step of the arthroplasty, affirm selection of a final combination of implants made virtually by the user, or confirm that all bone preparation is complete and ready for use of trial implants or for the final combination of implants to be implanted on the bone.

8. The system of claim 1, wherein the processor is configured to overlay an image of the bone on the updated model, wherein the image is derived from imaging the bone of the patient.

9. The system of claim 8, wherein the overlay is displayed on a mixed reality device.

10. The system of claim 8, wherein one of the image of the bone or the updated model is displayed semi-transparent.

11. The system of claim 10, wherein areas of correspondence or lack of correspondence between the image of the bone and the updated model are highlighted by at least one of a color difference or indicia.

12. The system of claim 1, further comprising a navigation tool configured to couple to a reamer, wherein the processor, based upon a position of the navigation tool when mounted to the reamer, determines the position of the intramedullary canal of the bone.

13. The system of claim 12, wherein the processor is configured to intraoperatively register the intramedullary canal of the bone using the navigation tool for the arthroplasty.

14. A system for performing a robotic revision knee arthroplasty, the system comprising:
  a reamer;
  a navigation tool configured to couple to the reamer; and
  a robotic surgical device including;
  a processor configured to:
  intraoperatively receive position data regarding a position of the navigation tool when coupled to the reamer after a primary implant has been removed from a bone of a patient,
  determine based upon the position data a position of an intramedullary canal of the bone based upon the position of the navigation tool,
  output to a user interface for display the position of the intramedullary canal for use during the robotic revision knee arthroplasty, wherein the display of the position of the intramedullary canal includes display of the intramedullary canal relative to a virtual replication of the bone of the patient and relative to a virtual representation of one or more revision implants with the the one or more revision implants superimposed on the virtual replication of the bone of the patient, and
  controlling the robotic surgical device to perform the robotic revision knee arthroplasty based upon the position of the intramedullary canal.

15. The system of claim 14, wherein the processor is configured to based upon the determined position of the intramedullary canal:
  select from a database having a plurality of mean models of a corresponding bone a mean model that comprises a best match based upon at least the position of the intramedullary canal;
  generate an updated model by altering the mean model to fit an anatomy of the bone of the patient based upon at least the position of the intramedullary canal; and
  output to the user interface for display the updated model for use during the robotic revision knee arthroplasty.

16. The system of claim 15, wherein the updated model shows the position of the intramedullary canal as an axis on the updated model, and wherein the updated model virtually replicates in at least two dimensions the bone of the patient.

17. The system of claim 15, wherein the updated model shows a plurality of landmarks including the intramedullary canal as a combination of one or more points and at least one axis, and wherein the combination of one or more points and at least one axis are reproduced on the updated model of the patient.

18. The system of claim 17, wherein the updated model shows a degree of confidence of the updated model matching an anatomy of the bone of the patient at the plurality of landmarks.

19. The system of claim 18, wherein the processor is configured via the user interface to issue a warning that based upon a virtual selection by L user regarding one or more of an offset of a stem, a size of the stem or a size of a bone interfacing feature that a breakage of the bone is likely to occur if such selection is implemented during the robotic revision knee arthroplasty, and wherein the processor is configured via the user interface to prompt the user to one or more of: remind the user a step of the robotic revision knee arthroplasty has been missed, confirm completion of each step of the robotic revision knee arthroplasty, affirm selection of a final combination of implants made virtually by the user, or confirm that all bone preparation is complete and ready for use of trial implants or for the final combination of implants to be implanted on the bone.

\* \* \* \* \*